United States Patent
Chiao

(10) Patent No.: US 6,654,664 B1
(45) Date of Patent: Nov. 25, 2003

(54) MULTIMEDIA AND SCENT STORAGE MEDIUM AND PLAYBACK APPARATUS

(75) Inventor: Dah-Shiarn Chiao, New York, NY (US)

(73) Assignee: MultiSen Technology, Inc., New York, NY (US)

( * ) Notice: Subject to any disclaimer, the term of this patent is extended or adjusted under 35 U.S.C. 154(b) by 0 days.

(21) Appl. No.: 09/593,219

(22) Filed: Jun. 14, 2000

(51) Int. Cl.[7] .......................... G06F 17/00; G03B 21/32
(52) U.S. Cl. .......................... 700/239; 700/241; 352/85
(58) Field of Search ................... 700/239, 241, 700/265, 231; 422/5, 108, 123; 352/85

(56) References Cited

U.S. PATENT DOCUMENTS

| | | | |
|---|---|---|---|
| 2,540,144 A | | 2/1951 | Stern |
| 2,813,452 A | * | 11/1957 | Laube ...................... 352/38 X |
| 2,905,049 A | * | 9/1959 | Laube ...................... 352/85 X |
| 4,556,539 A | * | 12/1985 | Spector ................... 422/125 X |
| 4,603,030 A | | 7/1986 | McCarthy |
| 4,617,147 A | | 10/1986 | Shinbani |
| 4,629,604 A | | 12/1986 | Spector |
| 4,761,437 A | | 8/1988 | Christie |
| 4,804,821 A | | 2/1989 | Glucksman |
| 4,880,774 A | | 11/1989 | Joukou et al. |
| 4,905,112 A | | 2/1990 | Rhodes |
| D313,018 S | | 12/1990 | Funabashi |
| 5,023,020 A | | 6/1991 | Machida et al. |
| 5,071,621 A | | 12/1991 | Tokuhiro et al. |
| 5,097,376 A | | 3/1992 | Khan |
| 5,150,722 A | | 9/1992 | Rutherford |
| 5,175,791 A | | 12/1992 | Muderlak et al. |
| 5,192,342 A | | 3/1993 | Baron et al. |
| D338,204 S | | 8/1993 | Takao |
| 5,314,669 A | | 5/1994 | Hamilton |
| D349,496 S | | 8/1994 | Sato |
| 5,398,070 A | * | 3/1995 | Lee ...................... 348/553 X |
| 5,429,180 A | | 7/1995 | Nishino et al. |
| 5,460,787 A | | 10/1995 | Colon |
| 5,480,591 A | | 1/1996 | Lagneaux et al. |
| 5,484,472 A | | 1/1996 | Weinberg |
| 5,503,332 A | | 4/1996 | Glenn |
| 5,565,148 A | | 10/1996 | Pendergrass, Jr. |

(List continued on next page.)

FOREIGN PATENT DOCUMENTS

| | | |
|---|---|---|
| WO | WO 00/15268 | 3/2000 |
| WO | WO 00/15269 | 3/2000 |

OTHER PUBLICATIONS

Derwent Publication; 1994–032881; Copyright Derwent Information LTD.

Primary Examiner—Gene O. Crawford
(74) Attorney, Agent, or Firm—David M. O'Neill

(57) ABSTRACT

The multimedia and scent storage medium described herein comprises a multimedia storage region for storing multimedia information; a scent storage region for storing multiple scents; scent identification information for identifying which scents are stored in the scent storage region; and scent recovery information stored in the multimedia storage region for sequencing recovery of scents stored in the scent storage region to coincide with audio and/or video information stored in the multimedia region. The integrated system described herein comprises a multimedia and scent storage medium and a multimedia player and scent recovery system for use in conjunction with the multimedia and scent-bearing medium. The multimedia and scent recovery system comprises a multimedia playback system for recovering the multimedia information stored in the multimedia storage regions of the multimedia and scent storage medium; a scent recovery system for recovering scents stored in the scent storage region of the multimedia and scent storage medium; and user input and control means for permitting the user of the integrated system to input commands for controlling the playback of multimedia information and recovery of scents stored in the multimedia and scent-bearing medium.

66 Claims, 17 Drawing Sheets

U.S. PATENT DOCUMENTS

| | | | |
|---|---|---|---|
| 5,577,156 | A | 11/1996 | Costello |
| 5,590,769 | A | 1/1997 | Lin |
| 5,591,409 | A | 1/1997 | Watkins |
| 5,716,431 | A | 2/1998 | von Glehn |
| 5,724,256 | A * | 3/1998 | Lee et al. ............... 700/285 X |
| 5,734,590 | A | 3/1998 | Tebbe |
| 5,742,256 | A | 4/1998 | Wakabayashi |
| 5,781,188 | A * | 7/1998 | Amiot et al. ............... 345/723 |
| 5,805,768 | A | 9/1998 | Schwartz et al. |
| 5,813,614 | A | 9/1998 | Coffee |
| D399,202 | S | 10/1998 | Kanatani |
| 5,848,727 | A | 12/1998 | Leo et al. |
| D405,082 | S | 2/1999 | Shibata |
| 5,887,118 | A | 3/1999 | Huffman et al. |
| D408,408 | S | 4/1999 | Ito et al. |
| 5,939,033 | A | 8/1999 | Kendall et al. |
| D413,887 | S | 9/1999 | Renk |
| 5,949,522 | A | 9/1999 | Manne |
| 5,963,302 | A | 10/1999 | Wittek |
| 5,972,290 | A | 10/1999 | De Sousa |
| D416,897 | S | 11/1999 | Ishii et al. |
| 6,004,516 | A | 12/1999 | Rasouli et al. |
| 6,004,666 | A | 12/1999 | Hornig et al. |
| 6,024,783 | A | 2/2000 | Budman |
| 6,025,902 | A | 2/2000 | Wittek |
| 6,041,023 | A | 3/2000 | Lakhansingh |
| 6,044,200 | A | 3/2000 | Hirdes |
| 6,044,202 | A | 3/2000 | Junkel |
| 6,053,738 | A | 4/2000 | Ivey, Jr. |
| 6,069,851 | A | 5/2000 | Fenner |
| D427,988 | S | 7/2000 | Haney |
| D430,444 | S | 9/2000 | Allsop et al. |
| D431,543 | S | 10/2000 | Yuyama |
| 6,282,458 | B1 * | 8/2001 | Murayama et al. ..... 700/239 X |
| 6,338,818 | B2 | 1/2002 | Budman |
| 6,357,726 | B1 | 3/2002 | Watkins |
| 6,426,778 | B1 * | 7/2002 | Valdez, Jr. ................... 348/461 |
| 6,430,582 | B1 * | 8/2002 | Duncombe ............... 715/500.1 |

* cited by examiner

MULTIMEDIA AND SCENT STORAGE MEDIUM AND PLAYBACK APPARATUS

FIELD OF THE INVENTION

The invention relates to multimedia systems having scent-dispersing capability, and more particularly to a multimedia and scent storage medium for use in conjunction with an integrated multimedia playback and scent recovery system.

BACKGROUND OF THE INVENTION

Multimedia sources heretofore usually have been limited to audio or visual media. For example, the public is widely familiar with television, high fidelity audio, FM radio, and more recently, the Internet (which typically is audio-visual in format). As a result, the public has been limited to audio or visual stimulation. There has not been widespread media available for providing an olfactory ("scent") stimulation, particularly scent media that are intended to operate in synchronism with audio or visual sources. Thus users are prevented from experiencing a complete multi-sensory experience that would provide an authentic virtual reality experience.

Known prior art is deficient for many reasons. For example, the prior art shows little or no appreciation for the need to identify scent sources stored on media so that multiple scents stored in them may be recovered in a pre-programmed sequence. Other prior art is designed for use in large auditoriums or movie theaters and comprise multiple, separate and expensive components that are impractical for personal or home use. The prior art also shows no appreciation of the desirability to provide user-specifiable scent sequences for use in combination with audio or visual multimedia sources.

More specifically, U.S. Pat. No. 5,887,118 to Huffman et al. teaches an olfactory card including a scent producing member. Although the olfactory card of Huffman can be used for personal applications, it suffers from several limitations that prevent it from being of widespread use. The most noticeable limitation is that it is intended for use with PCMCIA slots in portable computers. PCMCIA cards are noticeably small and provide little room for storing the volume of scents that would be required for use in home multimedia applications. Further, in order to properly operate with the PCMCIA interface, the olfactory card requires a separate interface and on-board processing hardware and, as a result, represents an expensive and complex solution.

In addition, the PCMCIA card of U.S. Pat. No. 5,887,118 includes both the scent and the scent recovery apparatus in a single housing. Since the scent-recovery scent apparatus and associated electronics are relatively expensive, a user is presented with a dilemma. After the scent has been exhausted, the user either has to dispose of the PCMCIA card and purchase a new one with fresh scent, or send the PCMCIA card to a commercial entity for refilling. Either of these are less acceptable than an inexpensive disposable alternative. Further, Huffman et al. does not teach any means for editing pre-programmed scent recovery sequences so that a user may "customize" scent recovery sequences for use with known multimedia sources.

U.S. Pat. No. 6,004,516 to Rasouli et al. discloses a scent-bearing disk and associated playback apparatus. The system disclosed in U.S. Pat. No. 6,004,516 shows no appreciation of scent recovery and sequencing problems. For instance, there is no teaching of how separate scents on the disk are tagged so that they can be rapidly and accurately accessed during playback of multimedia content so that the scent recovery sequence coincides with the multimedia content.

U.S. Pat. No. 4,629,604 describes a player for a multi-aroma cartridge with individual electric heaters. The player disclosed therein provides no scent identification information for various replacement cartridges, nor is it an Internet-compatible device. Not having any tag or scent identification information limits the flexibility of the player disclosed in U.S. Pat. No. 4,629,604.

U.S. Pat. No. 5,949,522 describes a device that can deliver various combinations of scent in rapid succession to a user's nose in conjunction with videographic images or sounds. Through proper control of valves and compressed air, the system described in U.S. Pat. No. 5,949,522 can use liquid fragrance without heating. U.S. Pat. No. 5,949,522 shows no appreciation of the need for tag or fragrance identification information to control the sequential recovery of fragrances from the fragrance containers. This limits the modes of operation and in turn the flexibility of the system. Furthermore, the whole system requires an uncomfortable and unsanitary nose tube.

U.S. Pat. No. 5,591,409 describes a method and apparatus for "metered spray" aroma delivery system for use with an entertainment system. The method and apparatus disclosed in U.S. Pat. No. 5,591,409 uses liquid fragrance without heating, and a limited number of fragrance containers without tag or scent identification information. This again limits the flexibility of operation of the device.

U.S. Pat. No. 6,053,738 describes an apparatus for reproducing smells and flavors using a cylindrical housing containing smell and flavor cartridges. U.S. Pat. No. 6,053,738 provides no tag information for future smell and taste replacements.

U.S. Pat. No. 5,565,148 describes a multiple aroma delivery apparatus with a plurality of separate cylindrically-shaped chambers. Limiting the arrangement of chambers and valves also decreases the variety of scents deliverable by the system.

U.S. Pat. No. 5,734,590 describes a device comprising a plurality of stimulus generators including a scent generator, with a micro-encapsulated scent carrier or a block of spray tubes. The utility signal source is from a separate recording medium. The system disclosed in U.S. Pat. No. 5,734,590 provides no tag or scent identification information for the scent carrier and lacks the ability to be re-programmed.

U.S. Pat. No. 6,025,902 describes a process for increasing the sensual perception of visual, acoustic,and odor stimulation in a theater U.S. Pat. No. 5,963,302 also describes a process for increasing the sensual perception of visual, acoustic, and scent stimulation in a theater, as well as various scent storing and releasing arrangements.

U.S. Pat. No. 6,024,783 describes a multimedia-linked apparatus for delivery of real-time or stored aroma. The aroma-producing system is a multi-chamber mechanism. The aroma emitting material is individually placed above each heater in each releasing chamber, and each chamber has it own air exhausting unit and a controlled opening door.

However, the system disclosed in U.S. Pat. No. 6,024,783 is based on scent or aroma carriers (i.e., card, disk, cartridge, container, or cylinder) that do not carry any tag or scent identification information within or on the scent or aroma carriers. Without any tag or scent identification information, the control device of the prior art cannot receive the tag information of scents or aroma. Thus the scents cannot be recovered in a pre-programmed sequence.

Providing tag or scent identification information for the scent or aroma carriers with a controller would generate more variety and precision with respect to scent or aroma recovery in a very cost-efficient way. In addition, the multimedia information recovered from the multimedia medium of the scent or aroma carriers would create another option for users, as a stand-alone multimedia playback and scent recovery device. The prior art shows no appreciation of these modes of operation.

There are different methods and apparatus for impregnating scent medium on a disk or a card to make a Scent Disk or a Scent Card or a Scent Cartridge. For example, U.S. Pat. No. 5,939,033 describes a method and apparatus for impregnating solid materials (e.g. hydrogen peroxide) on a disk allowing conductive foil to conduct heat. U.S. Pat. No. 5,972,290 describes a process and apparatus for programmed scent delivery by piercing capsules of scented substrates and compounds embedded on a disk. U.S. Pat. No. 5,848,727 discloses a strip dispenser that is manually generated. U.S. Pat. No. 5,460,787 presents a method and apparatus for an insertable scented card. U.S. Pat. No. 6,044,202 describes an apparatus and method for a heated deodorizing scent card with a body of fragrance compound and an embedded plurality of individual and heat generating resistors operated via a thermistor.

There are also different methods and apparatus for improving scent cartridges. U.S. Pat. No. 5,314,669 describes a multi-layer cylindrical system to dispense different scents without changing the retaining carriage. U.S. Pat. No. 5,023,020 also describes a cylindrical receptor with plural containers for receiving -scents. U.S. Pat. No. 5,742,256 describes a computer-controlled metered-delivery device, which dispenses scents onto a rotating absorptive porous member.

There are different methods and apparatus for applying gas permeable membrane materials to control scent release. U.S. Pat. No. 5,150,722 describes a method for effecting the controlled release of fragrance in a relatively "long period." U.S. Pat. No. 5,480,591 describes a "naturally" diffusing diffuser with membranes on the flank.

With respect to recording media with scent, U.S. Pat. No. 5,097,376 describes a container with a fragrance material, in particular, a tape cassette with embedded scent. However, the embedded fragrance only serves for identification purposes and shows no appreciation of the use of multiple scents. U.S. Pat. No. 6,004,666 discloses a data carrier having fracturable microencapsulated scents releasable upon fracturing the micro-capsules.

Timing controlled scent diffusion methods have been used to diffuse scents in air, with some attempts to develop aroma-delivering apparatuses with timing control. U.S. Pat. No. 4,603,030 describes a scent-emitting system to propel scents in response to a programmed sequence of scents of predetermined duration. U.S. Pat. No. 5,175,791 describes a stepped power control fragrance diffuser with fragrance-emitting blocks within certain pre-programmed time period. U.S. Pat. No. 5,805,768 describes an apparatus with a rotating a plurality of receptacles for various scents, allowing the user to pre-select a variety of aroma to be delivered at pre-determined time intervals.

There have been some attempts to develop a neutralizing method to increase the sensitivity and perception level between scent releasing. U.S. Pat. No. 5,429,180 describes a process and apparatus for introducing refreshing-type aromatic agent between relaxing-type aromatic agents in a repetition of cycles. This prior art does not provide neutralizing or masking function that synchronizes with multimedia presentation.

Thus, a multimedia and scent recovery system that is capable of storing multiple scents in sufficient quantity is desirable so that a user may use it in a home environment in combination with a multimedia playback means to create a realistic virtual reality experience that may include audio or visual stimulation in combination with scent stimulation. A relatively simple storage medium that combines both multimedia information and multiple scents that would also facilitate a realistic virtual reality experience that may be repeated over and over again is also desired. In addition, an editing means that permits a user to depart from a pre-programmed scent recovery sequence in order so that the user may create a "customized" virtual reality experience, including multimedia and scent elements is also desired.

SUMMARY OF THE INVENTION

The limitations of the prior art are overcome in the following embodiments of the present invention. A first embodiment of the present invention comprises a multimedia and scent storage medium, further comprising a multimedia storage region for storing multimedia information; a scent storage region for storing multiple scents; scent identification information for identifying which scents are stored in the scent storage region; and scent recovery information stored in the multimedia storage region for sequencing recovery of scents stored in the scent storage region to coincide with audio and/or video information stored in the multimedia region. The multimedia information stored in the multimedia region may comprise audio, video, textual, graphical or photographic information.

A variation of the first embodiment comprises a multimedia and scent-bearing medium having a plurality of recessed three-dimensional regions for storing separate scents; inert storage media deposited within the regions for storing separate scents; and a gas permeable membrane placed over upwardly-facing openings of the recessed three-dimensional regions. The gas permeable membrane may comprise a microporous or macroporous polymer.

Another variation of the first embodiment of the present invention comprises the multimedia and scent-bearing media of the foregoing embodiments in combination with scent recovery sequence information for controlling the sequential recovery of scents stored in the scent storage region.

In a further variation of the first embodiment of the present invention, the scent recovery sequence information of the preceding embodiments further facilitates the simultaneous recovery of scent and multimedia information to provide an immersive, multi-sensory experience. In this further variation scent-neutralizing or scent-masking materials are also stored in the multimedia and scent-bearing medium. The scent-neutralizing or scent-masking material is used to mask previous scents recovered from the multimedia and scent-bearing medium before additional scent are released.

In yet another variation of the first embodiment of the present invention, the multimedia and scent-bearing medium comprises a housing having multiple storage slots; a plurality of scents stored within each slot; and a scent identification means. Each canister has a release valve for facilitating the release of scents from the canister. The scent identification means identifies which scents are stored in which slots. Bar codes may be used as the scent identification means.

Further variations of the first embodiment of the present invention overcome the limitations of the prior art with respect to the storage of volatile scents. In one embodiment the multimedia and scent-bearing medium is stored in a storage case having overlapping seals to prevent scent from escaping from the scent storage region. In another embodiment a gas impermeable membrane is placed over the gas permeable membrane covering the recessed three-dimensional regions (each of which stores a separate scent) of the multimedia and scent-bearing medium to prevent scent from escaping from the recessed three-dimensional regions.

A second embodiment of the present invention comprises an integrated system having a multimedia and scent storage medium and a multimedia player and scent recovery system for use in conjunction with the multimedia and scent-bearing medium. The multimedia playback and scent -recovery system of the second embodiment comprises a multimedia playback system for recovering the multimedia information stored in the multimedia storage regions of the multimedia and scent storage medium; a scent recovery system for recovering scents stored in the scent storage region of the multimedia and scent storage medium; and user input and control means for permitting the user of the integrated system to input commands for controlling the playback of multimedia information and recovery of scents stored in the multimedia and scent-bearing medium.

A variation of the second embodiment comprises a multimedia player having an optical (e.g. CD, DVD, or bar code) or magnetic playback system (e.g. floppy, hard disk, or tape) for retrieving the encoded multimedia information. The audio signal recovered from the multimedia information can be played back through a speaker system that is connected to an amplifier system. The video signal recovered from the multimedia information can be played back through a visual display system (e.g. a monitor or a LCD).

Another variation of the second embodiment of the present invention comprises an interactive playback system to edit the pre-programmed scent recovery sequence information retrieved from the multimedia and scent-bearing medium for controlling the sequential recovery of scents stored in the scent storage region. The editing function of the present invention allows a user to create a user-specified scent recovery sequence by editing the scent recovery sequence information recovered from the multimedia and scent-bearing medium. Using the editing function, a user may alter the order of scent recovery; change the duration of recovery of individual scents, or substitute other scents for those specified by the pre-programmed scent recovery sequence information. The editing means also permits a user to create entirely new scent recovery sequences to be used in conjunction with multimedia information.

In a further variation of the second embodiment of the present invention, the scent recovery system may comprise single or multiple, movable heating elements. The scent recovery system converts the scent recovery sequence information recovered from the multimedia and scent storage medium into control signals for controlling the operation of the heating elements. Upon receiving the control signal, the heating elements (e.g. laser or infrared) will move to a predetermined position so that they may heat and thereby release the heat-releasable scents stored within the scent-bearing medium. Through a ductwork immediately adjacent to the multimedia and scent-bearing medium, a fan will facilitate the venting of scents to the user of the integrated system.

Yet another variation of the second embodiment of the present invention comprises an input connection for accepting a multimedia signal from a remote source. The remote multimedia source may comprise radio, television, or satellite transmitters, or publicly switched telephone networks (PSTN) or cable systems, or LAN, or WAN, or a computer. The remote multimedia information may comprise separately-recoverable segments and may further comprise audio, video textual, graphical or photographic information.

Still further variations of the second embodiment of the present invention overcome the limitations of the prior art with respect to the variety of scents storage media. By retrieving the tagging, scent recovery sequence, and the multimedia information from the multimedia medium or remote source and storing all of this information in a local storage system, the present invention not only provides precise coupling between scents and scent recovery sequence information but also allows the user to edit or transmit specified scent recovery sequences and multimedia information to another user.

Thus, it is seen that embodiments of the present invention overcome limitations of the prior art. Known scent storage media do not include information identifying either which scents are stored or what sequence the scents are to be recovered from the scent storage media. In contrast, the present invention stores scent identification and scent recovery sequence information in the multimedia and scent storage medium, thereby permitting the synchronized recovery of multimedia information and scents stored in the multimedia and scent storage medium. This manner of operation provides an immersive, multi-sensory experience.

Other known scent storage media require complex circuitry, processing capability, and heating elements for releasing scent from the scent storage media. Such media are complex in construction, expensive to manufacture, and expensive to purchase. In contrast, the multimedia and scent storage medium of the present invention is designed to operate with an integrated multimedia playback and scent recovery system that includes playback and scent recovery hardware. In consequence, the multimedia playback and scent recovery hardware need not be positioned on the multimedia and scent storage medium. As a result, the multimedia and scent storage medium of the present invention is simple in construction, inexpensive to manufacture, and inexpensive to purchase.

There are no known, integrated multimedia playback and scent recovery systems. As a result, it is difficult, if not impossible, to create synchronized multimedia playback and scent recovery sequences that are repeatable. Further, it is also difficult to develop new synchronized multimedia playback and scent recovery sequences. In contrast, the multimedia playback and scent recovery system of the present invention is designed to operate with multimedia and scent storage media that store scent identification and scent recovery sequence information. As a result, a user of the multimedia playback and scent recovery system can "replay" synchronized multimedia and scent recovery sequences to provide an immersive, multi-sensory experience that is repeatable. Further, the multimedia playback and scent recovery system of the present invention further comprises scent recovery sequence information storage means, and scent recovery sequence information editing means. In contrast to the prior art, this feature of the present invention permits a user to edit pre-programmed multimedia playback and scent recovery sequences to create new, "custom," user-specified multimedia playback and scent recovery sequences. Further, this feature of the present invention also permits a user to create entirely new multimedia playback and scent recovery sequences.

BRIEF DESCRIPTION OF THE FIGURES

The above and other objects and advantages of this invention will be apparent upon consideration of the following detailed description, taken in conjunction with the accompanying drawings in which like reference characters refer to like elements throughout, and in which.

DETAILED DESCRIPTION OF THE PREFERRED EMBODIMENTS

The features and advantages of the present invention are illustrated in detail in the accompanying drawings, wherein like reference numbers refer to like elements throughout the drawings.

I. First Preferred Embodiment

Figure 1:
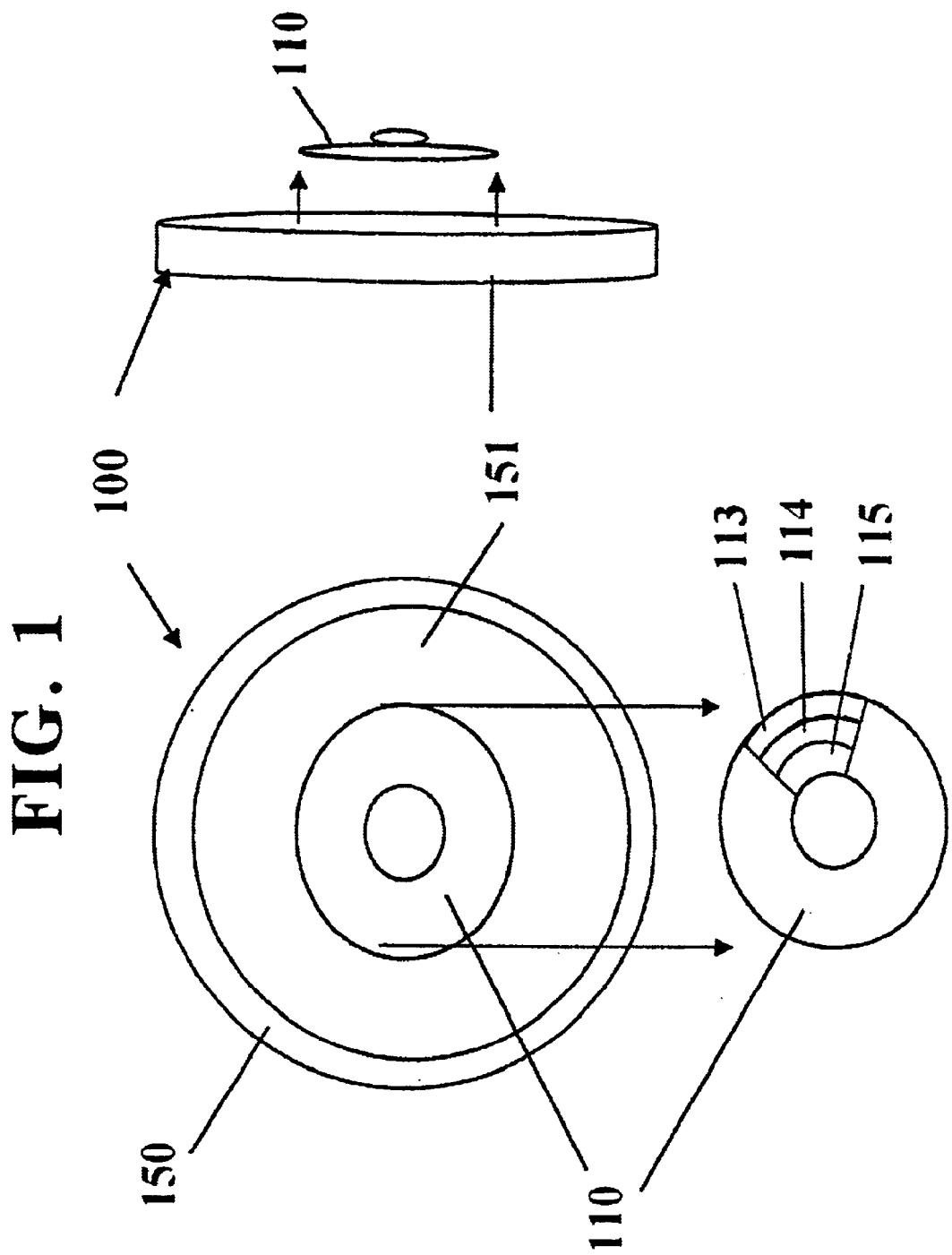
FIG. 1 depicts top and side views of a multimedia and scent-bearing medium 100 made in accordance with a first preferred embodiment of the present invention.
Figure 2A:
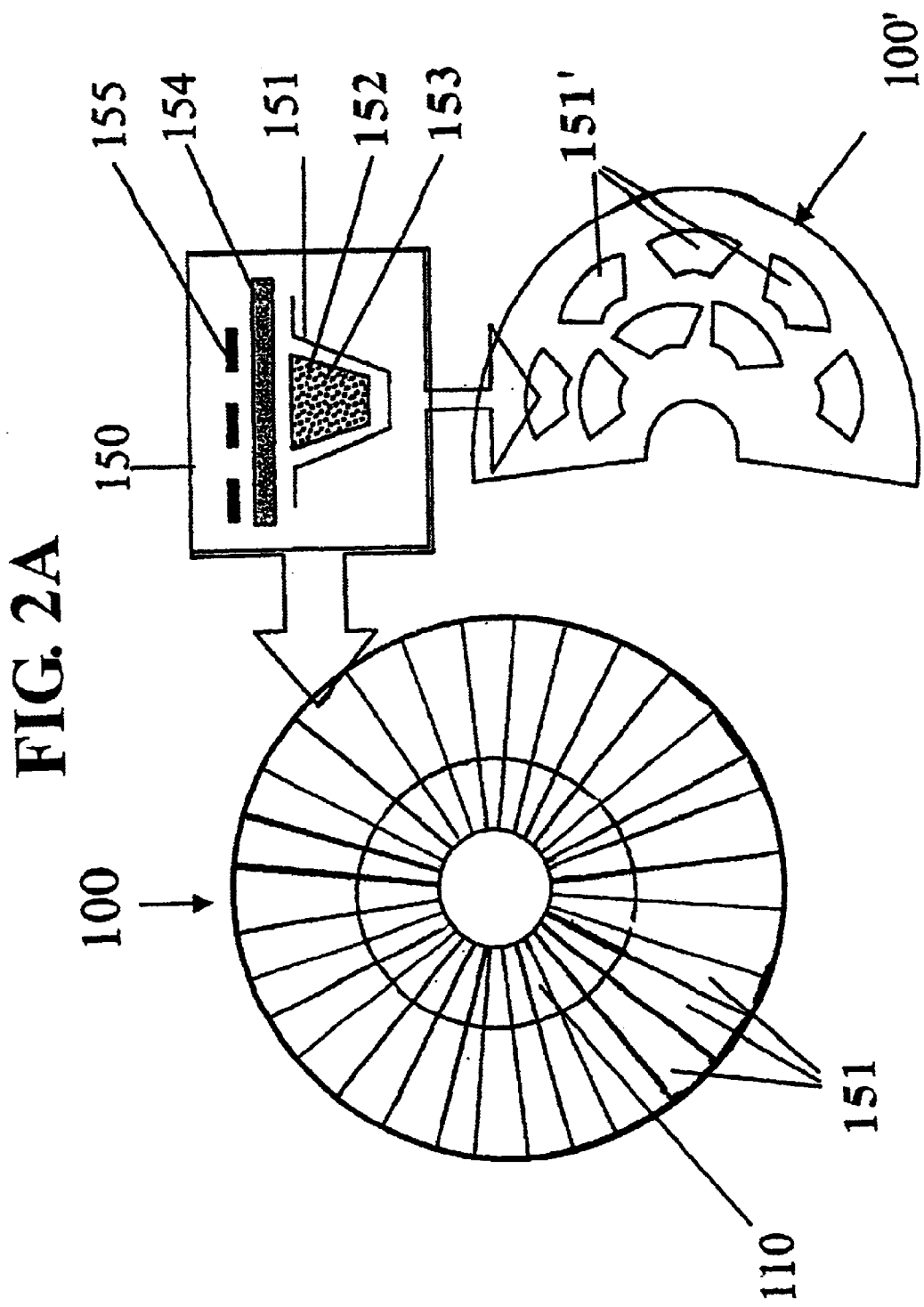
FIG. 2A depicts a top view of a multimedia and scent-bearing medium 100, and in particular a cross-sectional view of a scent-bearing medium 150, made in accordance with a first preferred embodiment of the present invention.

A first preferred embodiment of the present invention comprises a multimedia and scent-bearing medium 100 as depicted in FIGS. 1 and 2A. The multimedia and scent-bearing medium 100 comprises two elements: a multimedia storage medium 110 and a scent-bearing medium 150. The scent-bearing medium 150 further comprises a plurality of recessed three-dimensional regions 151 each for storing a separate scent.

Deposited within each three-dimensional region is an inert storage medium 152. The inert storage medium 152 is not reactive with the scents that will be stored within it. The three-dimensional region is formed in the plastic housing of the multimedia and scent-bearing medium 100. A plurality of radically extending three-dimensional regions are shown in the multimedia and scent-bearing medium 100 depicted in FIG. 2A. The three-dimensional regions may also take concentric forms 151' as shown in the partial view of the multimedia and scent-bearing medium 100' also shown in FIG. 2A. The inert storage medium 152 may be a polymer gel and may take other forms that are well known to those of ordinary skill in the art.

A scent 153 is stored in the inert storage medium 152 shown in the cross-sectional view of FIG. 2A. The scent 153 is preferably heat releasable. In addition, a gas permeable membrane 154 is placed over each recessed three-dimensional region 151. The gas permeable membrane 154 permits scent 153 to escape from the recessed three-dimensional region 151 when heated.

A gas impermeable membrane 155 is shown in ghost view in the cross-sectional view of FIG. 2A. The gas impermeable membrane 155 is used for sealing purposes and is preferably reusable. The gas impermeable membrane 155 prevents the scents 153 stored in recessed three-dimensional region 151 in the multimedia and scent-bearing medium 100 from escaping when the multimedia and scent-bearing medium 100 is not in use.

The multimedia information is stored in the multimedia storage medium 110 of the multimedia and scent-bearing medium 100. The multimedia storage medium 110 in the embodiments depicted in FIGS. 1 and 2A corresponds to the conventional CD-ROM recording format. The multimedia information can also be stored in the multimedia region 110 using other formats, for example, DVD. Utilization of the DVD format will provide for greater storage capacity. The multimedia information stored in the multimedia storage medium 110 may take many forms including, for example, video, audio, textual, graphical, and photographic. As shown in the audio and video embodiment depicted in FIG. 1, audio information is digitally encoded using well known digitally encoding formats in the region 113. Video information is also digitally encoded using well-known digitally encoding formats in the region 114.

Digital scent identification information and scent recovery sequence information are stored in the scent region 115. The digital scent identification information identifies which scents are stored in which recessed three-dimensional regions 151. The scent recovery sequence information is used to synchronize scent recovery with the playback of multimedia information stored in the multimedia region 110. For example, the scent recovery sequence information could be used to recover a gun powder scent to coincide with the canon shot recorded in an audio recording of Tchaikovsky's 1812 Overture. In another embodiment, the scent recovery sequence information could be used to recover flower scents stored in the scent storage region 151 recovered from scent storage medium 150.

The multimedia information encoded in the multimedia storage medium 110 preferably may be segregated into separately recoverable segments. This would be particularly useful for use with interactive playback systems (e.g., an interactive multimedia game). Particular scents or particular sequence of scents would be programmed to coincide with particular multimedia segments to give an immersive multi-sensory experience.

Figure 2B:
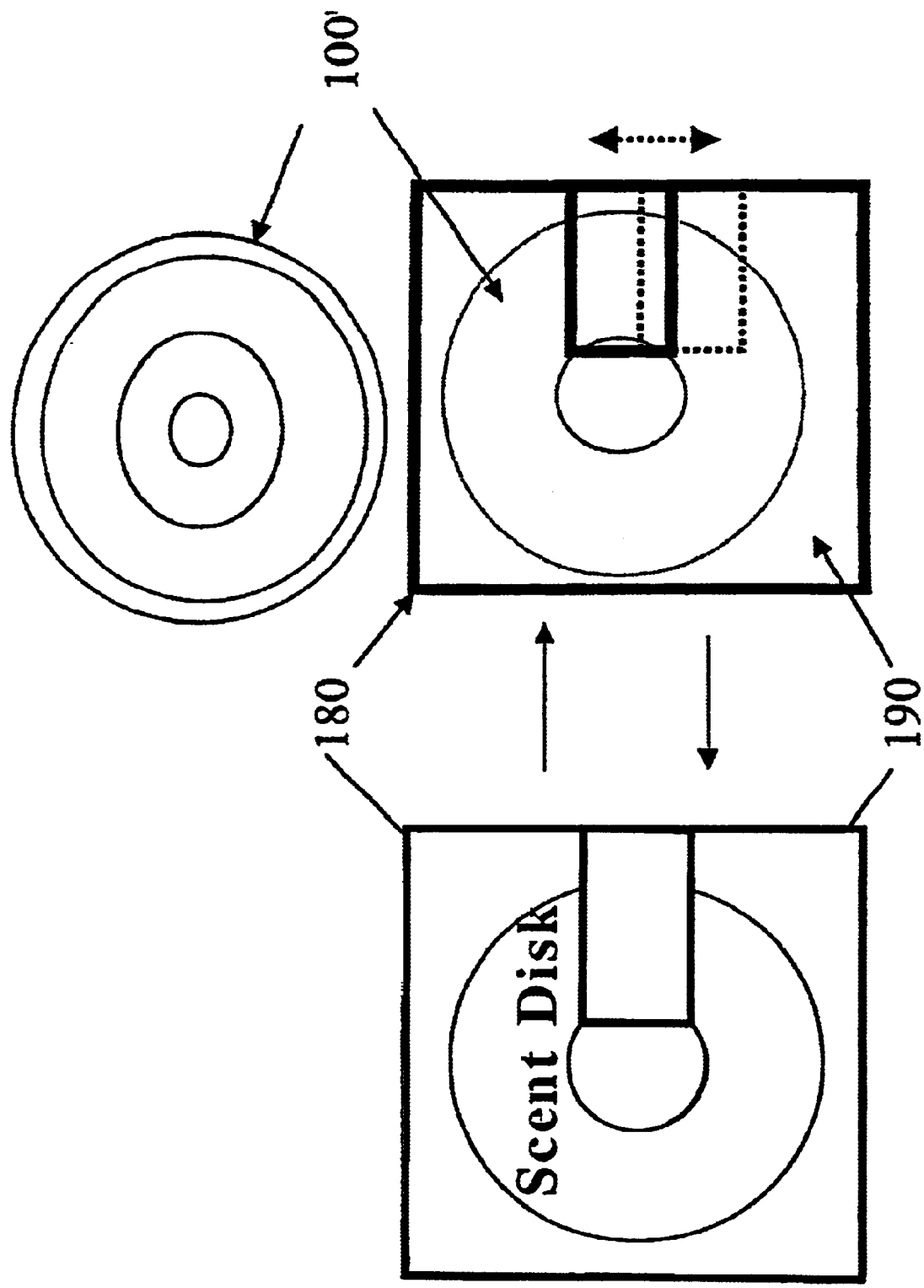
FIG. 2B depicts a multimedia and scent storage medium 100 placed in storage case 180 apparatus, and made in accordance with a first preferred embodiment of the present invention.

Preferably a storage case 180 having overlapping seals 190 is used to store the multimedia and scent-bearing medium 100 depicted in FIG. 2B. The overlapping seals 190 prevent scents from escaping from the multimedia and scent-bearing medium 100.

Figure 3:
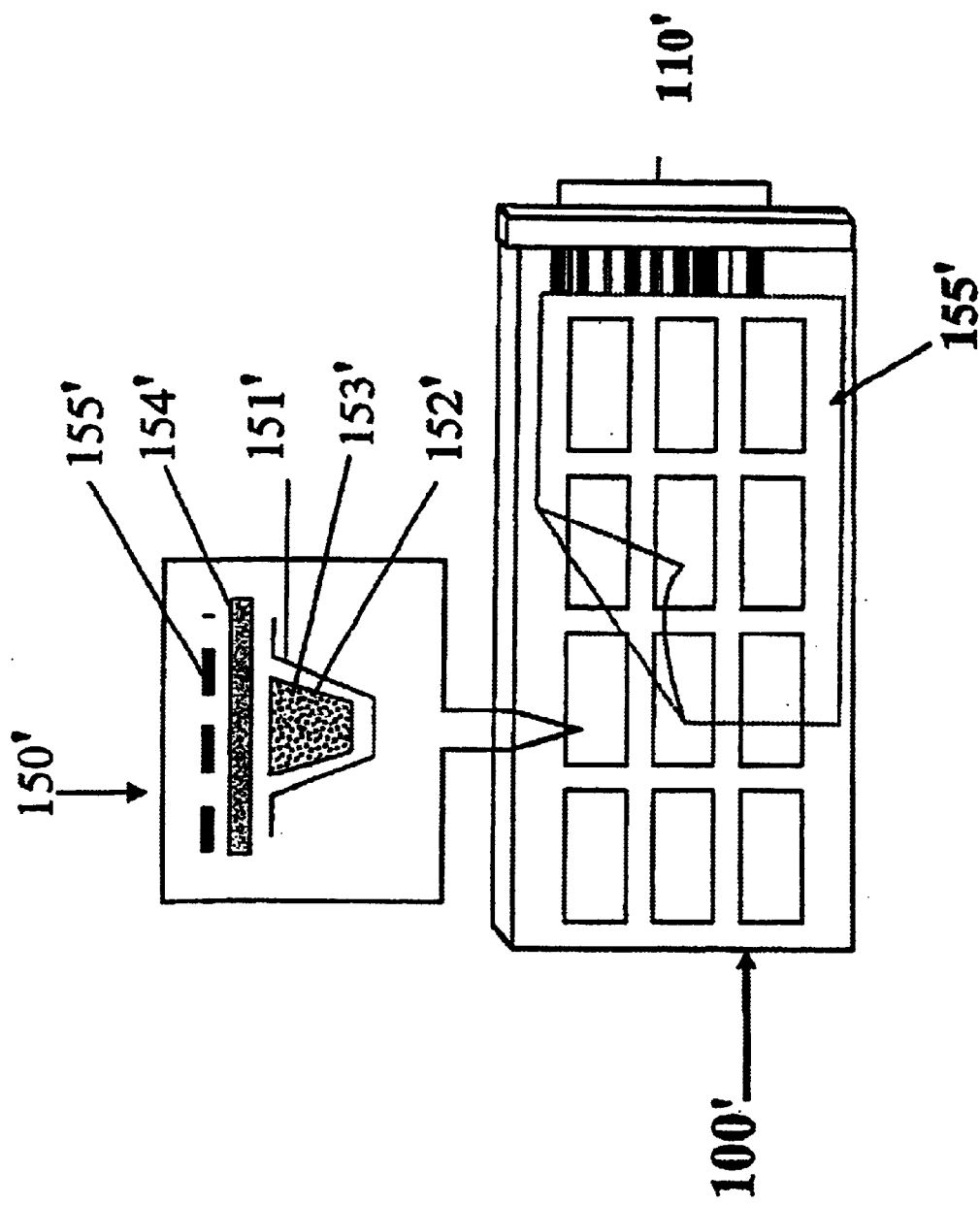
FIG. 3 depicts a top view of an alternate multimedia and scent-bearing medium 100', and a detail view of scent-bearing medium 150', made in accordance with a first preferred embodiment of the present invention.
Figure 4:
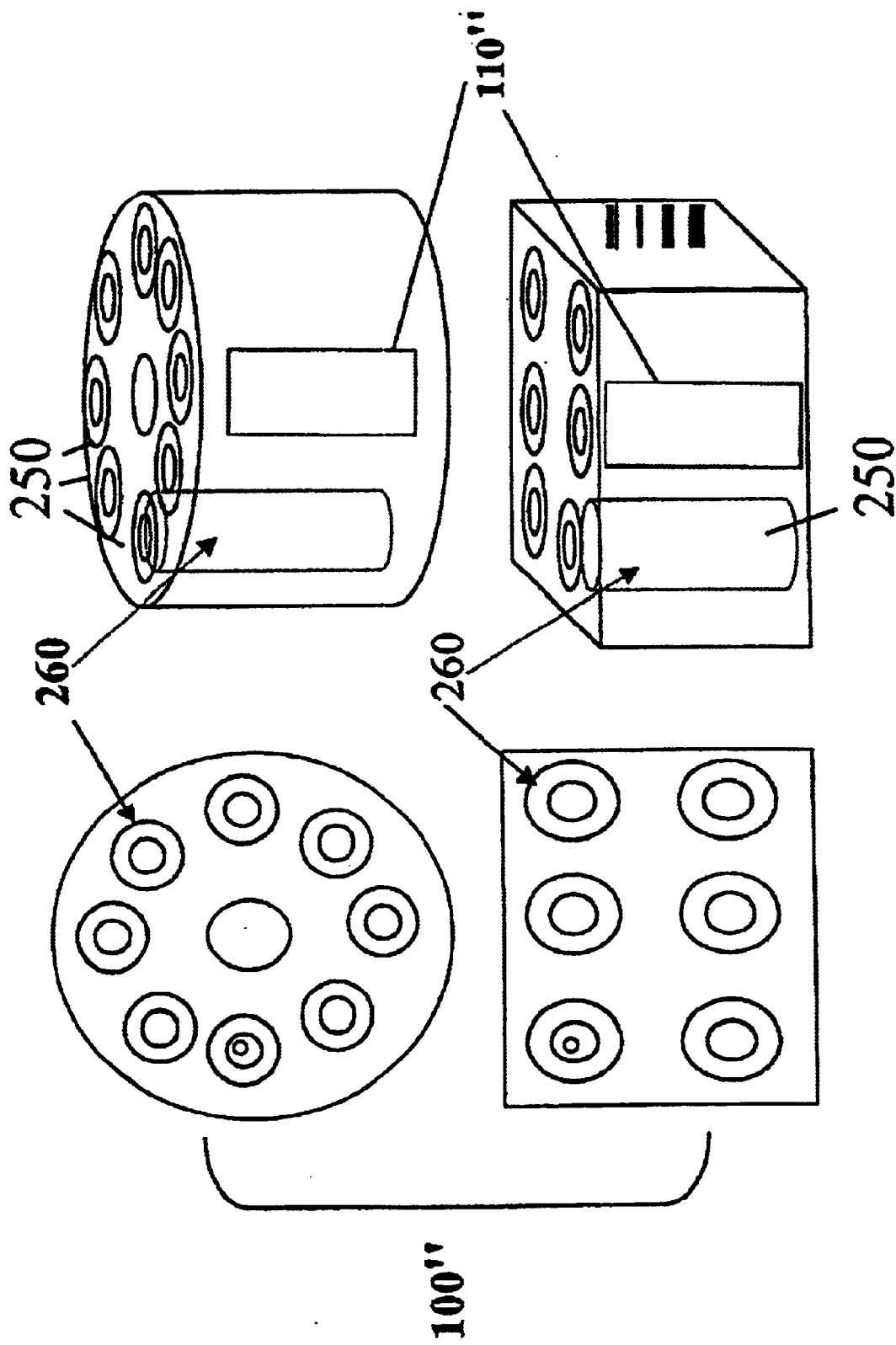
FIG. 4 depicts multiple views of an alternate multimedia and scent-bearing medium 100" made in accordance with a first preferred embodiment of the present invention.

In a variant of the first preferred embodiment shown in FIG. 3, the multimedia and scent-bearing medium 100' uses a magnetic memory in place of the optical storage medium depicted in FIGS. 1 and 2A. Information is recovered from magnetic memory electrically. As in the case of the first preferred embodiment, scent is stored in scent-bearing medium 150' in a plurality of recessed three-dimensional regions 151'. In this particular variant the regions take a rectangular form. The recessed three-dimensional regions 151' are also shown in cross-section in FIG. 3.

Also as in the case of the first preferred embodiment, scent 153' is stored in an inert storage medium 152'. The scent 153' is preferably heat releasable. In addition, a gas permeable membrane 154' is placed over each recessed three-dimensional region 151'. The gas permeable membrane 154' permits scent 153' to escape from the recessed three-dimensional region 151' when heated. A gas impermeable membrane 155' is shown in ghost view in the cross-sectional view of FIG. 3. The gas impermeable membrane 155' is used for sealing purposes and is preferably reusable. The gas impermeable membrane 155' prevents the scents 153' stored in recessed three-dimensional region 151' in the multimedia and scent-bearing medium 100' from escaping when the multimedia and scent-bearing medium 100' is not in use.

In another variant of the first preferred embodiment, the multimedia and scent storage medium 100" stores scent in a plurality of scent canisters 260. The scent canisters 260 are stored in a scent storage slot 250. Each canister has a release valve (not shown) of well-understood, conventional construction. Multimedia information is stored in high density, two-dimensional bar codes. The two-dimensional bar codes are also used to store scent identification and scent recovery sequence information to control the release of scents from the canisters 260.

The scent storage media and multimedia storage means described herein can be combined in various ways which are also within the scope of this invention. For example, scent canisters can be combined with other optical or magnetic multimedia storage formats.

II. Second Preferred Embodiment

Figure 5:
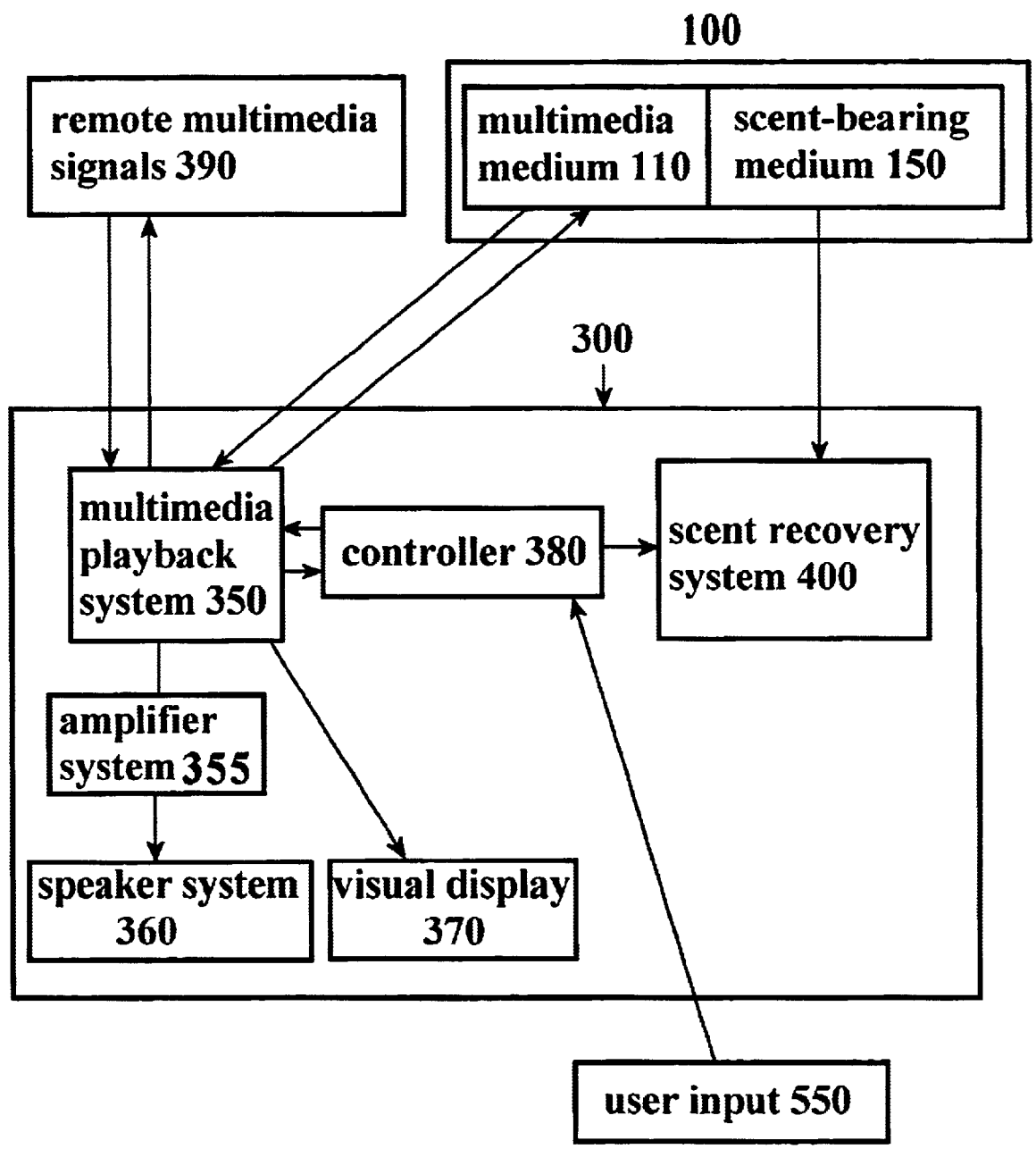
FIG. 5 depicts a conceptual block diagram showing an integrated system having a multimedia and scent storage medium and a multimedia playback and scent recovery system made in accordance with a second preferred embodiment of the present invention.
Figure 6:
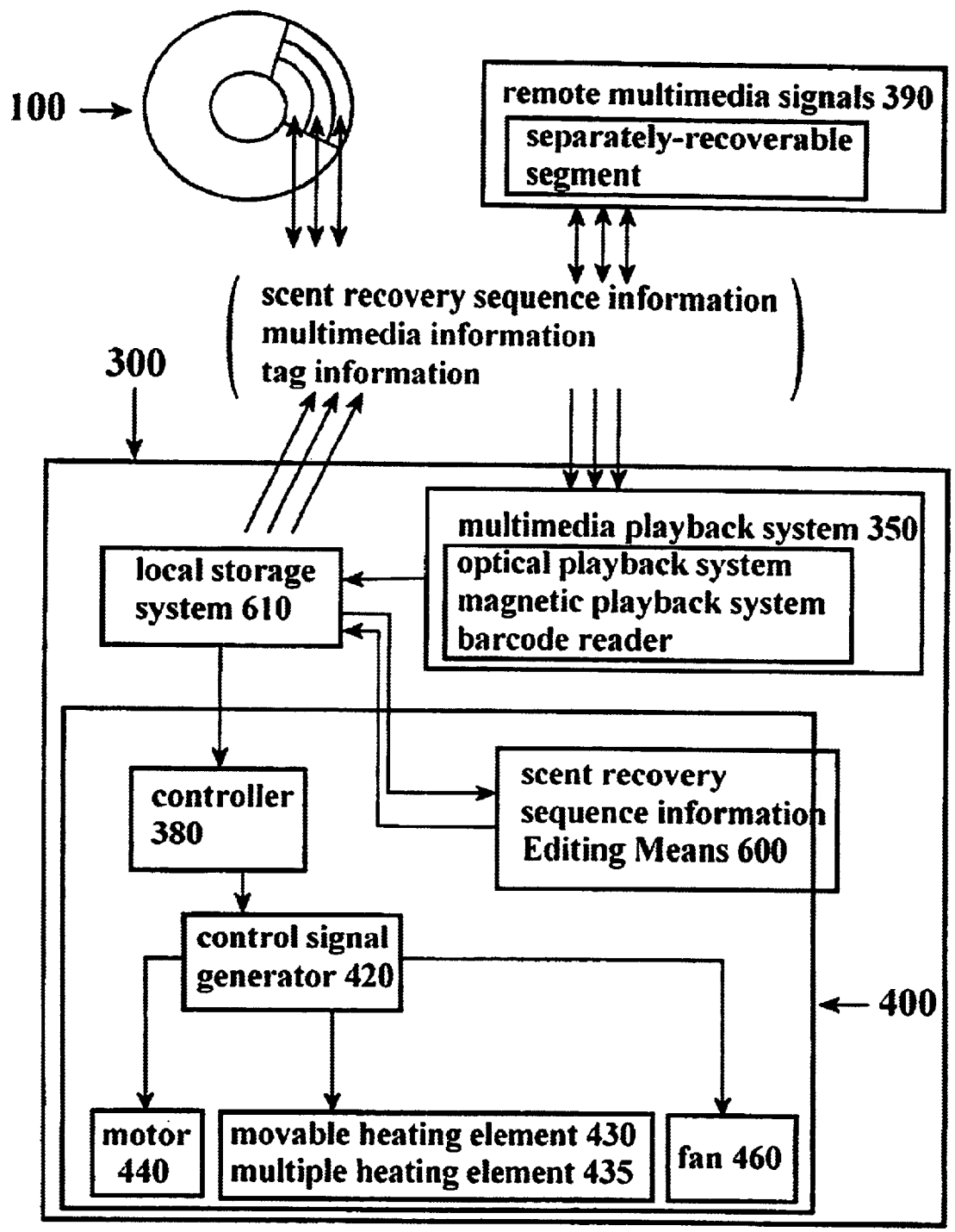
FIG. 6 depicts a conceptual block diagram of a scent recovery system 400 made in accordance with a second preferred embodiment of the present invention.

A second embodiment of the present invention comprises the combination of a multimedia and scent storage medium 100 and an integrated multimedia playback and scent recovery system 300 as shown in conceptual form in FIGS. 5 and 6. As in the case of the first embodiment, the multimedia and scent-bearing medium 100 of the second preferred embodiment comprises a multimedia storage medium 110 and a scent-bearing medium 150. The integrated multimedia playback and scent recovery system 300 comprises a multimedia playback system 350 and a scent recovery system 400. The multimedia playback system 350 recovers multimedia information from the multimedia storage medium 110. The multimedia playback system 350 converts audio information recovered from the multimedia storage medium 110 into an audio signal for amplification by an amplifier system 355 and for playback on a speaker system 360. Video information recovered from the multimedia storage medium 110 is converted into a video signal for playback on a video display 370.

The multimedia playback system 350 also recovers scent identification and scent recovery sequence information from the multimedia storage medium 110. This information is converted into a control signal by controller 380. The control signal generated by controller 380 is used to control the scent recovery system 400. Thus, the multimedia playback system 350 can be used to recover pre-programmed multimedia and scent recovery sequences stored on the multimedia and scent-bearing medium 100. In addition, the multimedia playback system 350 can also be used in conjunction with remote multimedia signals 390 which may be recovered from various sources, e.g., radio/broadcasting, satellite, Internet, a public switched telephone network (PSTN), a LAN, a WAN or a computer. These remote multimedia signals 390 may also include scent recovery sequence information. Thus, scents stored in the multimedia and scent-bearing medium 100 can be used in the second preferred embodiment either with multimedia signals stored in the multimedia and scent-bearing medium 100 or with remote multimedia signals 390 captured from a plurality of sources.

Figure 7:
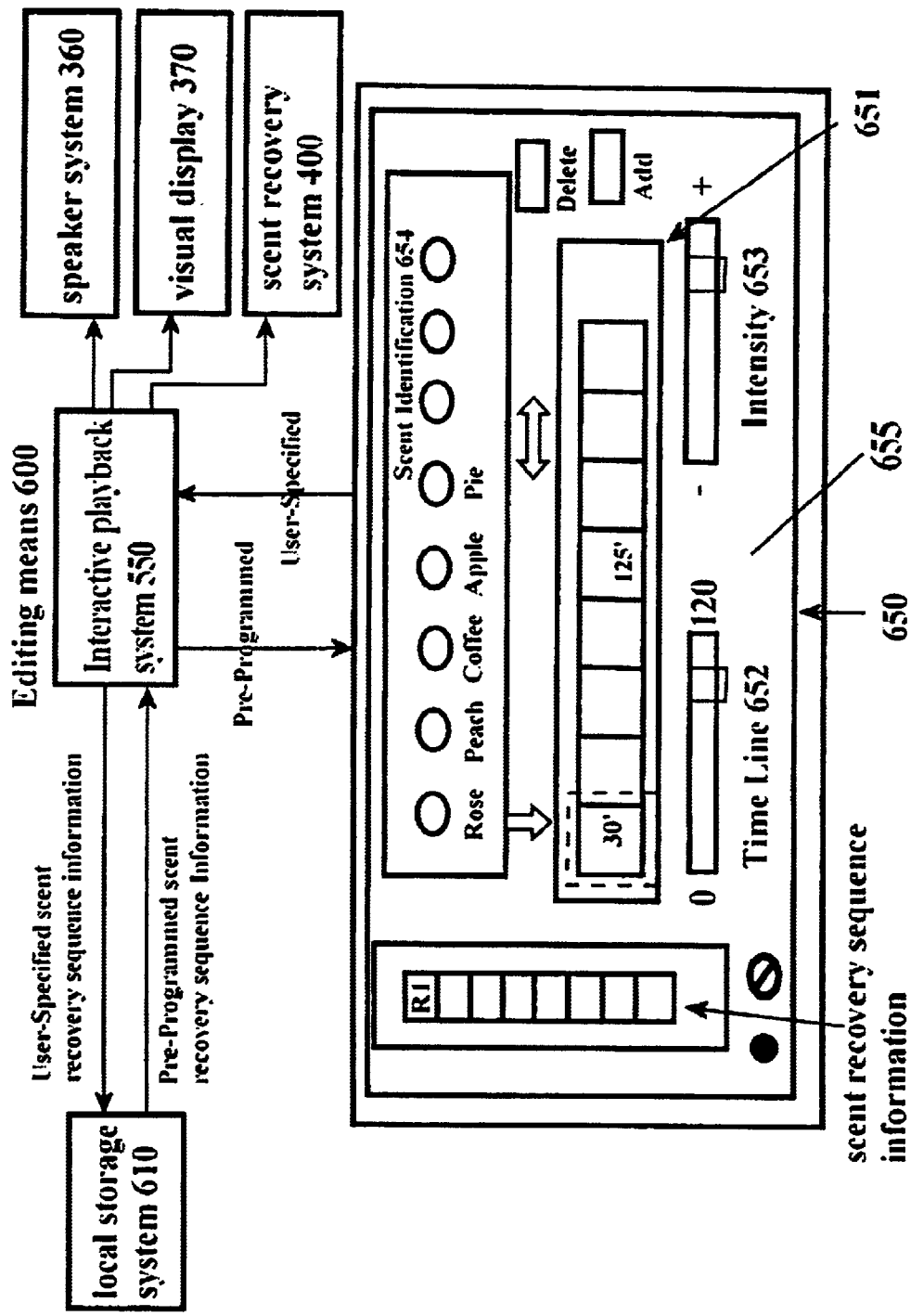
FIG. 7 depicts a conceptual block diagram illustrating the operation of editing means 600 and graphical user interface 650 made in accordance with a second preferred embodiment of the present invention.

The multimedia playback and scent recovery system 300 has several playback modes. For example, a user could simply "play back" pre-programmed multimedia and synchronized scent recovery sequences by depressing a start button to initiate the sequence. The multimedia playback and scent recovery system 300 also facilitates other playback modes. For example, the multimedia playback and scent recovery system 300 also includes editing means 600 as shown in FIGS. 6 and 7 for "customizing" pre-programmed multimedia and scent recovery sequences to accommodate user preferences. The editing means 600 comprises a local storage system 610 for storing the scent recovery sequence information recovered either from the multimedia and scent-bearing medium 100 or the remote source 390. Many types of local storage systems 610 may be used to store multimedia information, for example, a mini hard drive, a RAM, or a MP3.

The editing means 600 also comprises a graphical user interface 650 which is depicted in FIG. 7 and which may be displayed on the display system of the multimedia playback and scent recovery system 300. The graphical user interface 650 as depicted in FIG. 7 may take many forms within the scope of this invention. For example, the graphical user interface 650 may include a portion 651 that depicts in graphical form the multimedia segments for which scent recovery sequence information is created. The scent recovery sequence information will be edited on a multimedia segment by segment basis. The user would double click on which multimedia portion indicated in 651 he/she wishes to edit the pre-programmed scent recovery sequence information. Once the user has indicated the multimedia segment of interest, the editing means 600 will recall the scent recovery sequence information corresponding to the segment from memory and display it in region 651. The display in region 651 will comprise a combination of timeline 652, intensity 653 and scent identification information 654. The timeline 652 will indicate which scents will be recovered in what sequence, and for what duration. The intensity segment 653 effectively specifies the amount of heat that will be applied to the scent-bearing regions 151 of the multimedia and scent-bearing medium 100.

A Java platform, particularly its Abstract Windowing Toolkit (AWT) can be used to create custom graphical front ends 650. The AWT provides interfaces and classes for dealing with different types of events generated by AWT components. In addition, Java gives application programmers numerous tools for building professional, cutomizeable cross-platform GUIs (graphic user interface).

Alternatively, the graphical user interface 650 can be created using a "Windows" platform. The coded Application Interface (API) can be used to create custom graphical front ends. Some C++ applications already provide interfaces and classes for dealing with different types of events generated by API components.

The editing means 600 through the graphical user interface 650 permits a user to add scents, delete scents, overlap scents, increase the duration of scents, and decrease the duration of scents. Further, the editing means 600 permits a user to create an entirely new scent recovery sequence for use with multimedia segments.

Figure 8:
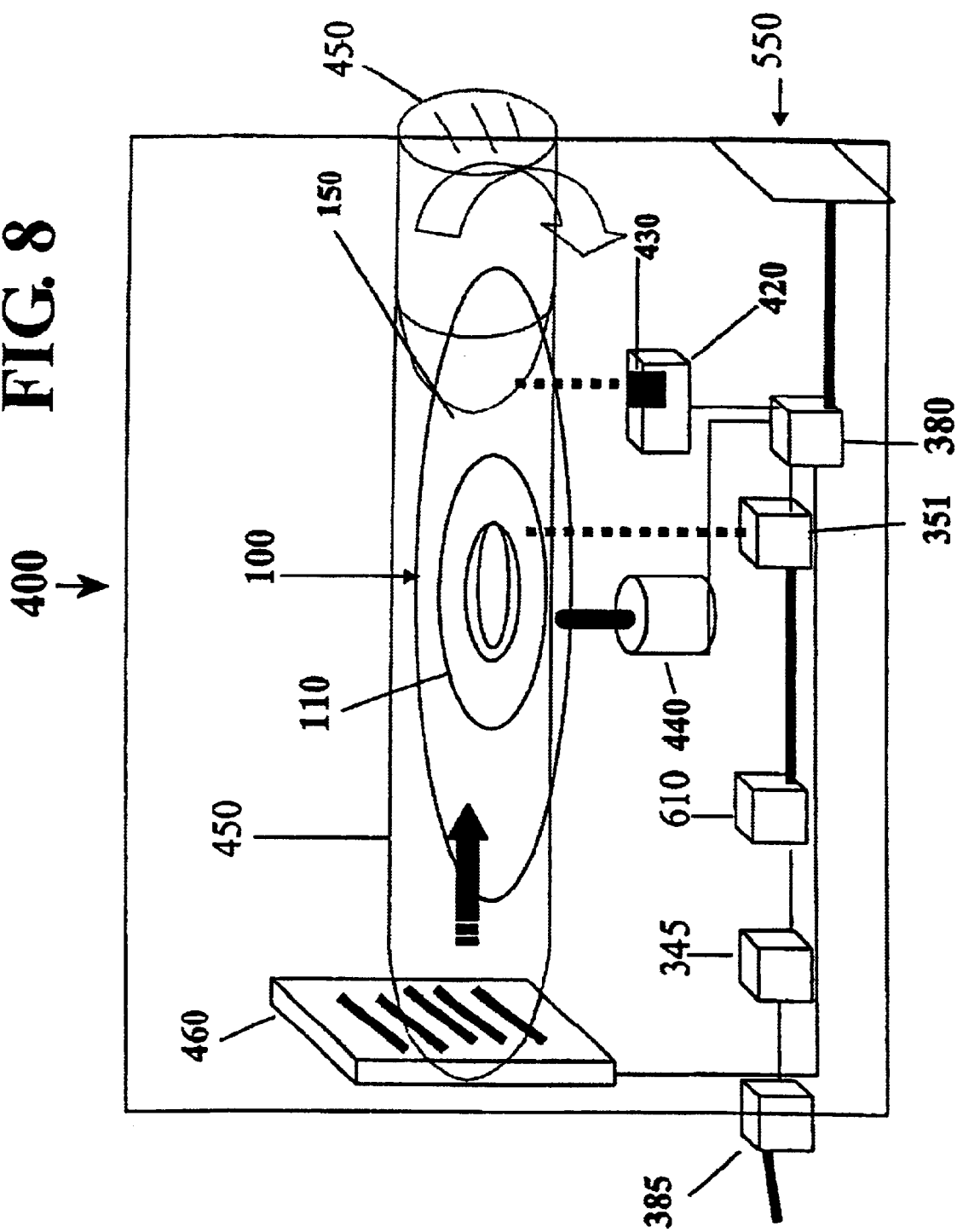
FIG. 8 depicts a schematic cross-sectional side view of a scent recovery system 400 made in accordance with a second preferred embodiment of the present invention for use in combination with multimedia and scent-bearing medium 100.

A cross-sectional side view of the scent recovery system 400 in accordance with a preferred second embodiment of the present invention is illustrated in FIG. 8. The scent recovery system 400 includes a movable heating element 430 (e.g. an Infrared or laser) which operates in response to control signals provided by the control signal generator 420 (e.g. Motorola's 8000 series microprocessor). After recovery of the scent recovery sequence information, tag information, and multimedia information; from the multimedia storage medium 110 to the local storage system 610, the controller 380 (e.g. CMOS PIC microcontroller) can use the tag information as reference data to couple event-related scent recovery signals which either have been transmitted from a remote multimedia source 390 or from the multimedia storage medium 110 to emit predetermined scent or combination of scents from the scent disk 140 by a ductwork 450 and controlled fan 460 (e.g. heat sink fan). A replaceable scent disk 140 emits a predetermined scent or a combination of scents when heated. Preferably, a predetermined scent from a scent-bearing medium 100 from the scent disk 140 is positioned directly above and/or in front of the movable heating element 430 by a controlled motor 440 (e.g. bipolar stepper motor).

Figure 9:
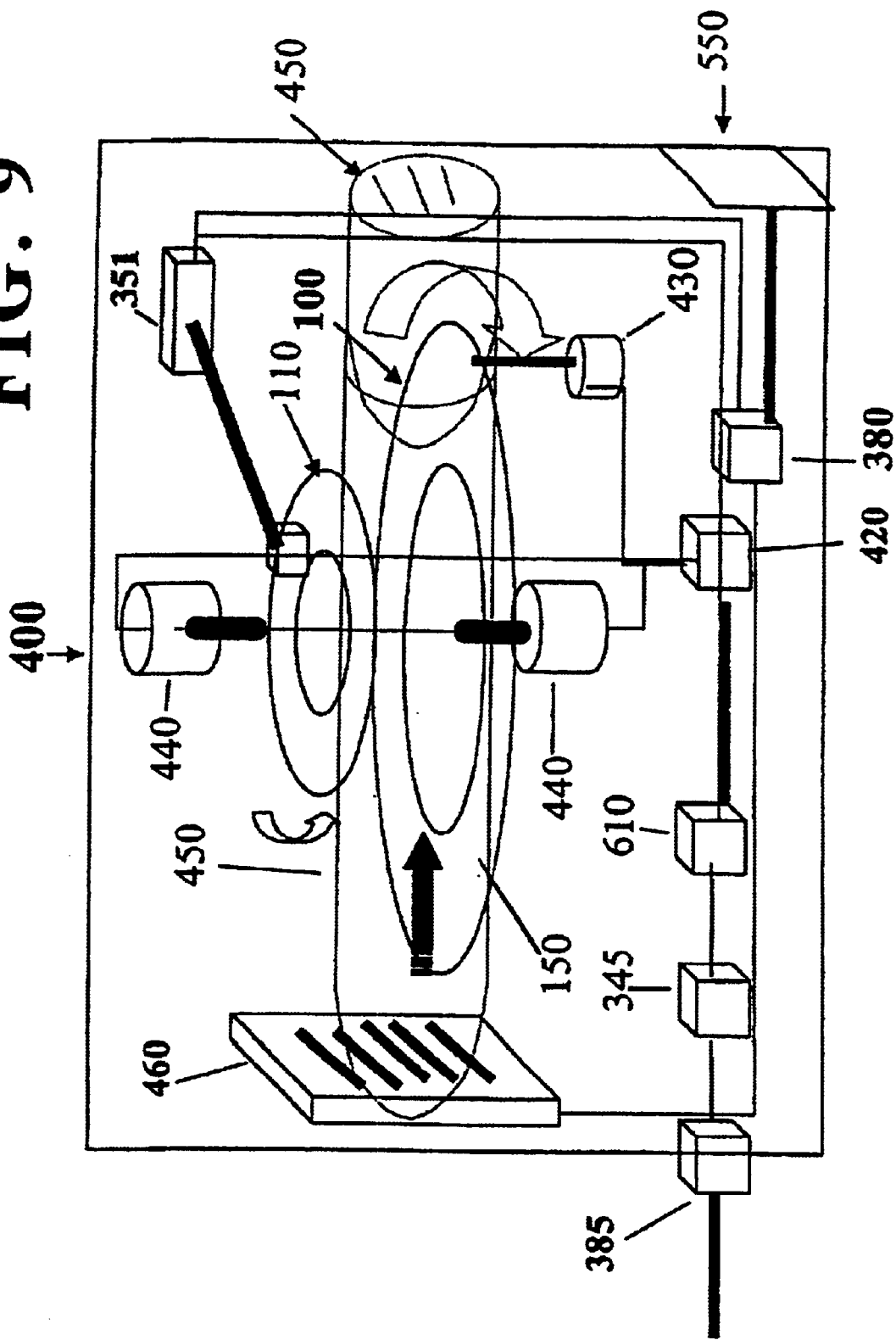
FIG. 9 depicts a schematic cross-sectional side view of an alternate scent recovery system 400 made in accordance with a second preferred embodiment of the present invention for use in combination with an alternate multimedia and scent-bearing medium 100.

In another preferred first and second embodiment of this invention shown in FIG. 9, a separable multimedia storage medium 110 (e.g. a compact disc) from scent-bearing medium 100 can actually operate as a separated entity by separated selectively controlled motor 440 without interruption to either unit.

Figure 10:
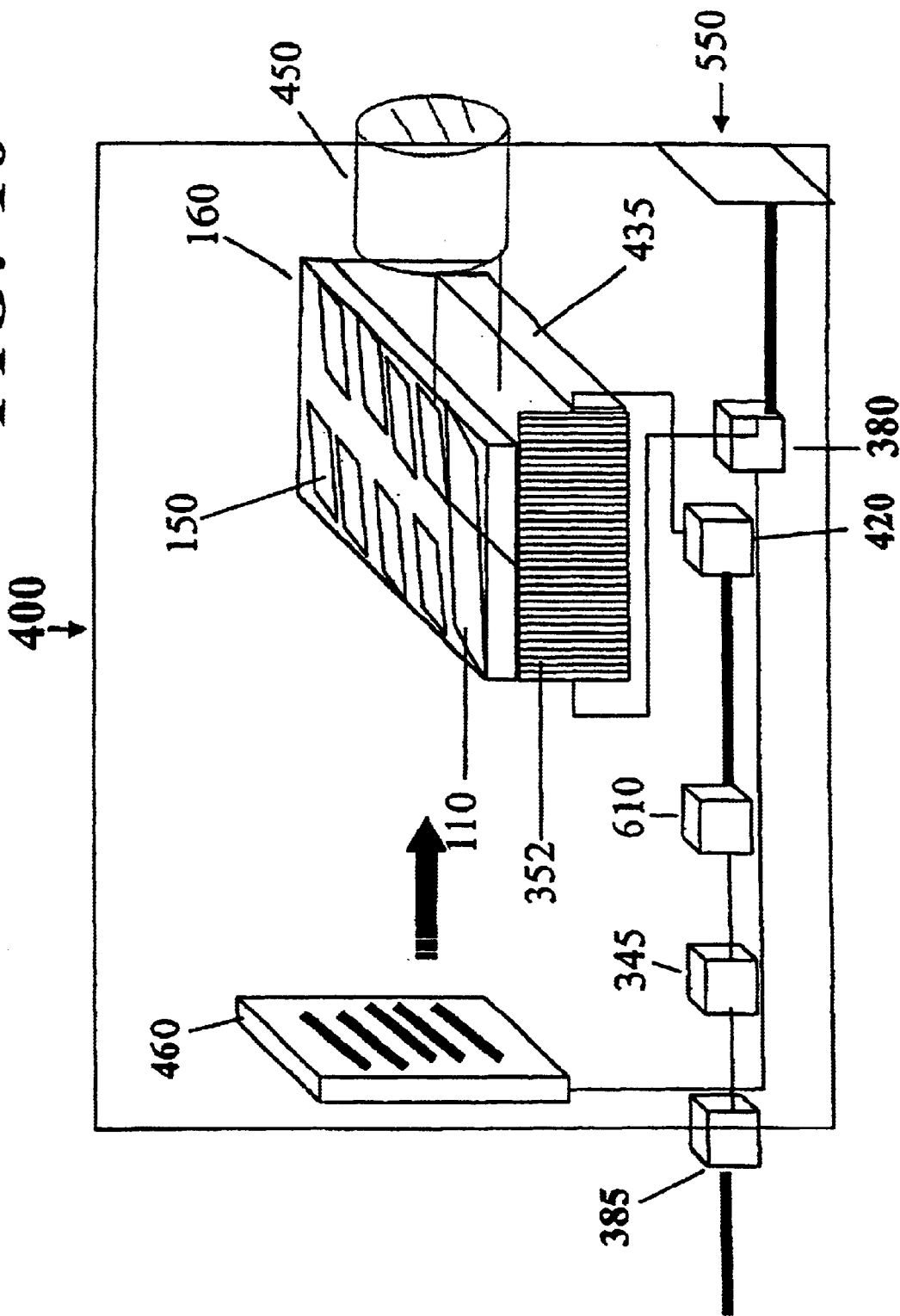
FIG. 10 depicts a schematic cross-sectional side view of an alternate scent recovery system 400 made in accordance with a second preferred embodiment of the present invention for use in combination with an alternate multimedia and scent-bearing medium 100.

Another yet cross-sectional side view of a scent recovery system 400 in accordance with a preferred second embodiment of the present invention is illustrated in FIG. 10. The scent recovery system 400 includes a multiple heating element 435 (e.g. an Infrared or laser or heating coil) which operates in response to control signals provided by the control signal generator 420. The insertable scent card 160 electronically connects with the controller 380 through a connector type magnetic playback system 352. After recovery of the scent recovery sequence information, tag information, and multimedia information from the multimedia storage medium 110 to the local storage system 610, the controller 380 can use the tag information as reference data to couple event-related scent recovery signals which either have been transmitted from a remote multimedia source 390 or from the multimedia storage medium 110 to emit predetermined scent or combination of scents from the scent card 160 by a ductwork 450 and controlled fan 460. A replaceable scent card 160 emits a predetermined scent or combination or scents when heated. Preferably, a pre-determined scent from a scent-bearing medium 100 from the scent card 160 is positioned directly above and/or in front of the multiple heating element 435 by selectively control signals.

Figure 11:
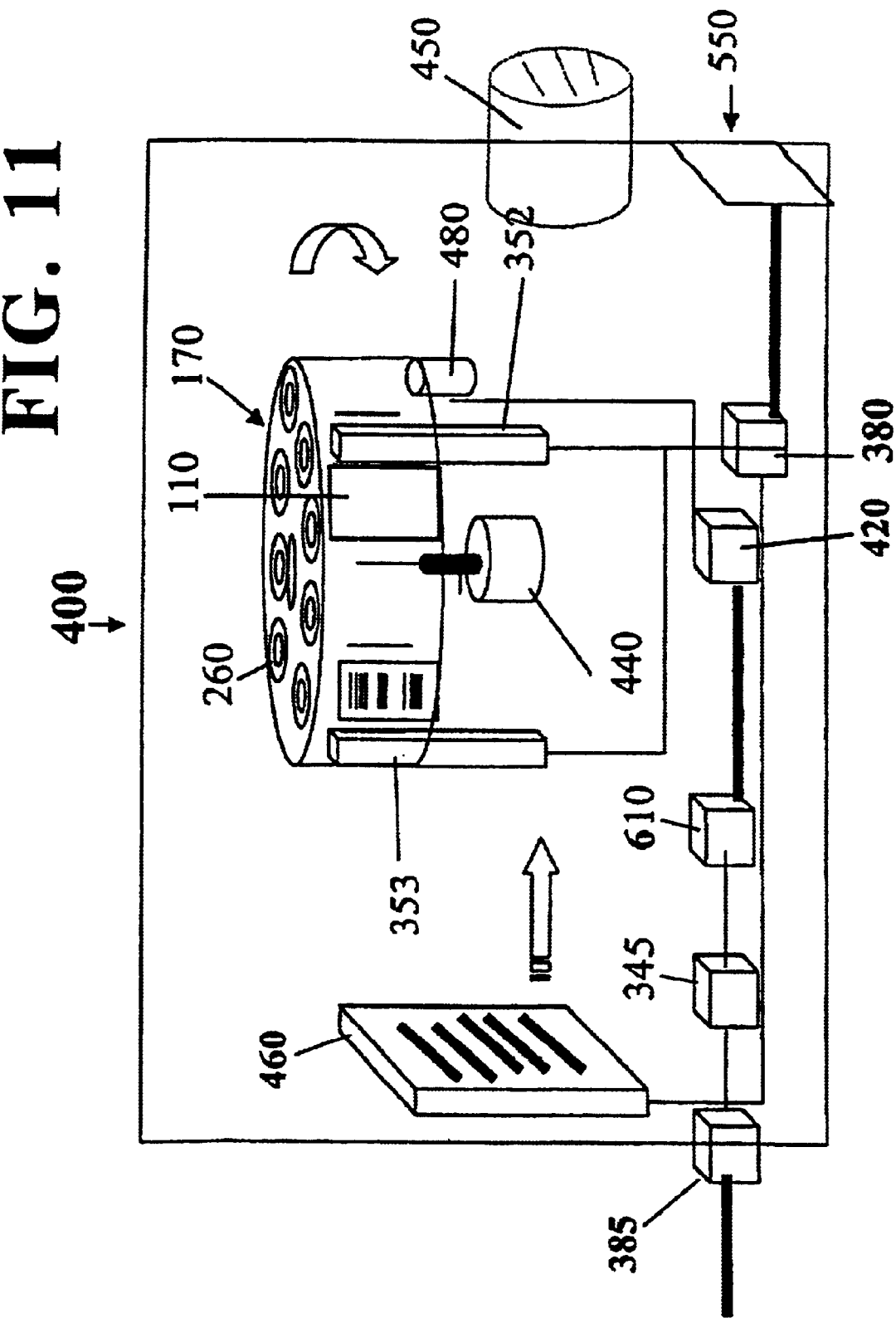
FIG. 11 depicts a schematic cross-sectional side view of an alternate scent recovery system 400 made in accordance with a second preferred embodiment of the present invention for use in combination with an alternate multimedia and scent-bearing medium 100.

A cross-sectional side view of a scent recovery system 400 in accordance with a preferred second embodiment of the present invention is illustrated in FIG. 11. The scent recovery system 400 includes a selectively controlled release valve system 480 (e.g. an ink-jet system) which operates in response to control signals provided by the control signal generator 420. A barcode reader 353 or magnetic playback system 352 will retrieve the scent recovery sequence information, tag information, and multimedia information from the scent identification 120 or multimedia storage medium 110 into the local storage system 610, the controller 380 can use the tag information as reference data to couple event-related scent recovery signals which either have been transmitted from a remote multimedia source 390 or from the multimedia storage medium 110 to emit predetermined scent or combination of scents from the cartridge 170 by a ductwork 450 and controlled fan 460. A replaceable scent cartridge 170 that emits a predetermined scent or a combination of scents when activated. Preferably, a predetermined scent from a canister 260 from the scent cartridge 170 is positioned directly in front of the ductwork 450 and controlled fan 460 by a controlled motor 440.

Figure 12:
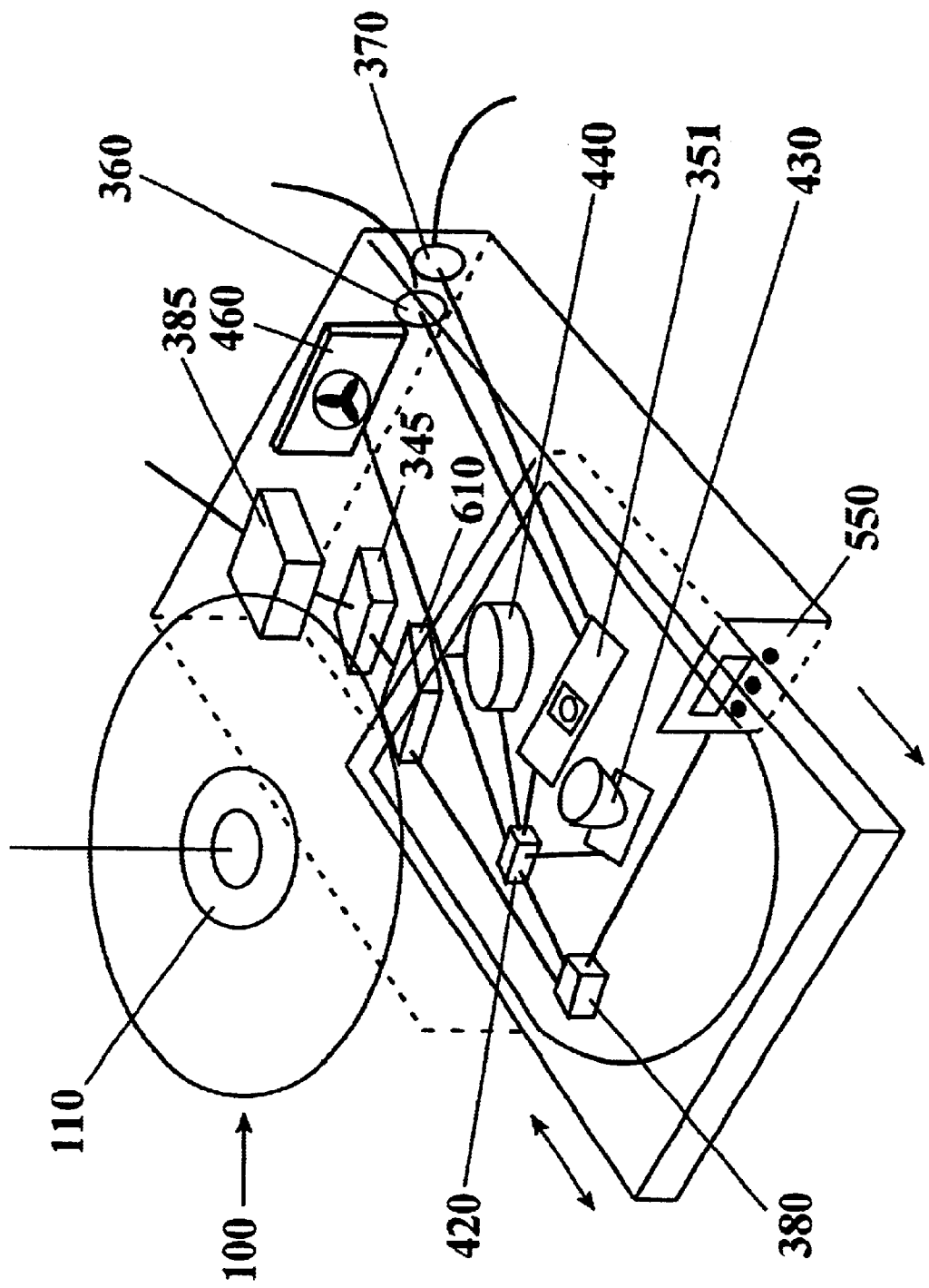
FIG. 12 depicts an exploded view of a multimedia playback and scent recovery system made in accordance with a second preferred embodiment of the present invention for use in combination with a multimedia and scent-bearing medium 100.
Figure 13:
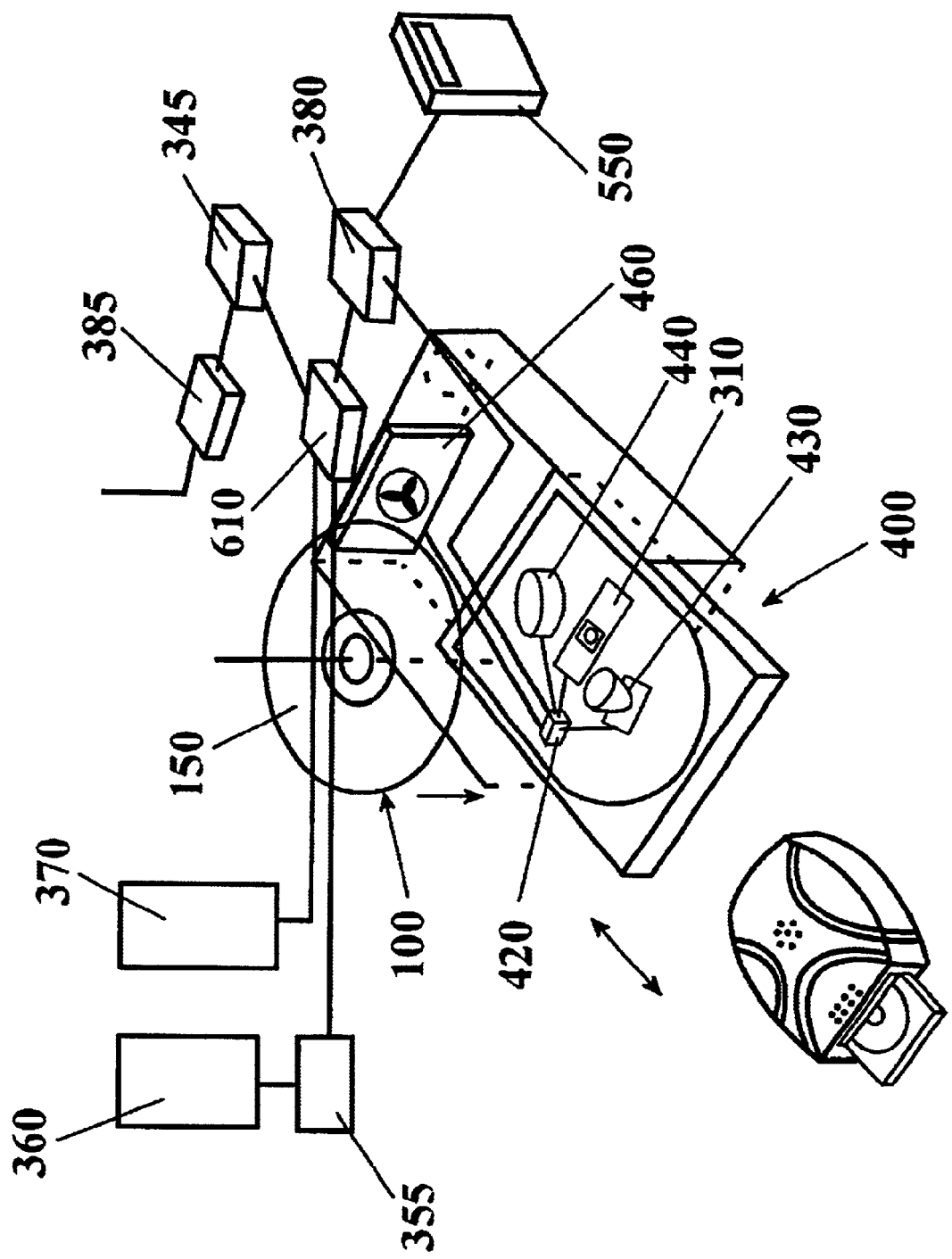
FIG. 13 depicts an exploded view of an alternate multimedia playback and scent recovery system made in accordance with a second preferred embodiment of the present invention for use in combination with an alternate multimedia and scent-bearing medium 100.

A multimedia playback and scent recovery system according to a preferred embodiment of the present invention is illustrated in FIG. 12. In this embodiment, the playback system comprises a scent disk 140 having not only scent-bearing medium 100 but also a multimedia storage medium 110 (e.g. a compact disc), with scent recovery sequence information, tag information, and multimedia information encoded thereon. A multimedia playback system 350 including an optical playback system 351 serves as the recovery system for accessing and processing the scent recovery sequence information, tag information, and multimedia information stored on the multimedia storage medium 110. The optical playback system 351 transmits scent recovery sequence information, tag information, and multimedia information to the controller 380 which encodes scent recovery sequence information into electronic signals prior to transmitting to the scent recovery system 400 or to a local storage system 610. A control signal generator 420 then retrieves the electronic signals to the scent recovery system 400.Another Another multimedia playback and scent recovery system according to a preferred embodiment of the present invention is illustrated in FIG. 13, wherein, the multimedia playback system 350 is separable from the scent recovery system 400.

Figure 14:
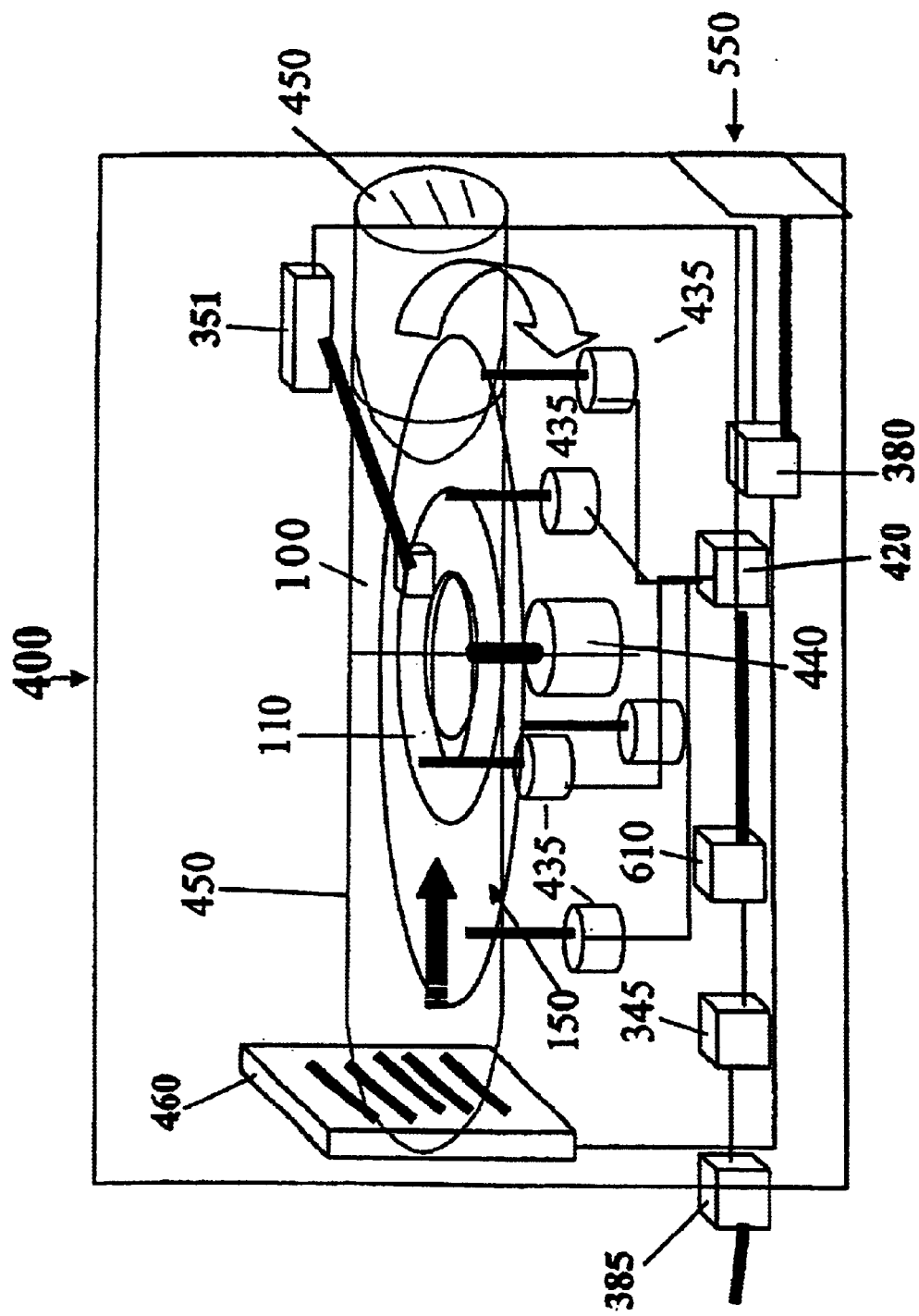
FIG. 14 depicts a schematic cross-sectional side view of an alternate scent recovery system 400 made in accordance with a second preferred embodiment of the present invention for use in combination with an alternate multimedia and scent-bearing medium 100.

A cross-sectional side view of a scent recovery system 400 in accordance with a preferred second embodiment of the present invention is illustrated in FIG. 14. The scent recovery system 400 includes a multiple heating element 435 (e.g. an Infrared or laser or heating coil) which operates in response to control signals provided by the control signal generator 420. After recovery of the scent recovery sequence information, tag information, and multimedia information from the multimedia storage medium 110 to the local storage system 610, the controller 380 can use the tag information as reference data to couple event-related scent recovery signals which either have been transmitted from a remote multimedia source 390 or from the multimedia storage medium 110 to emit predetermined scent or combination of scents from the scent disk 140 by a ductwork 450 and controlled fan 460. A replaceable scent disk 140 emits a predetermined scent or combination or scents when heated. Preferably, a plurality of predetermined scent from a scent-bearing medium 100 from the scent disk 140 are positioned directly above and/or in front of the multiple heating element 435 by selectively control signals.

Figure 15:
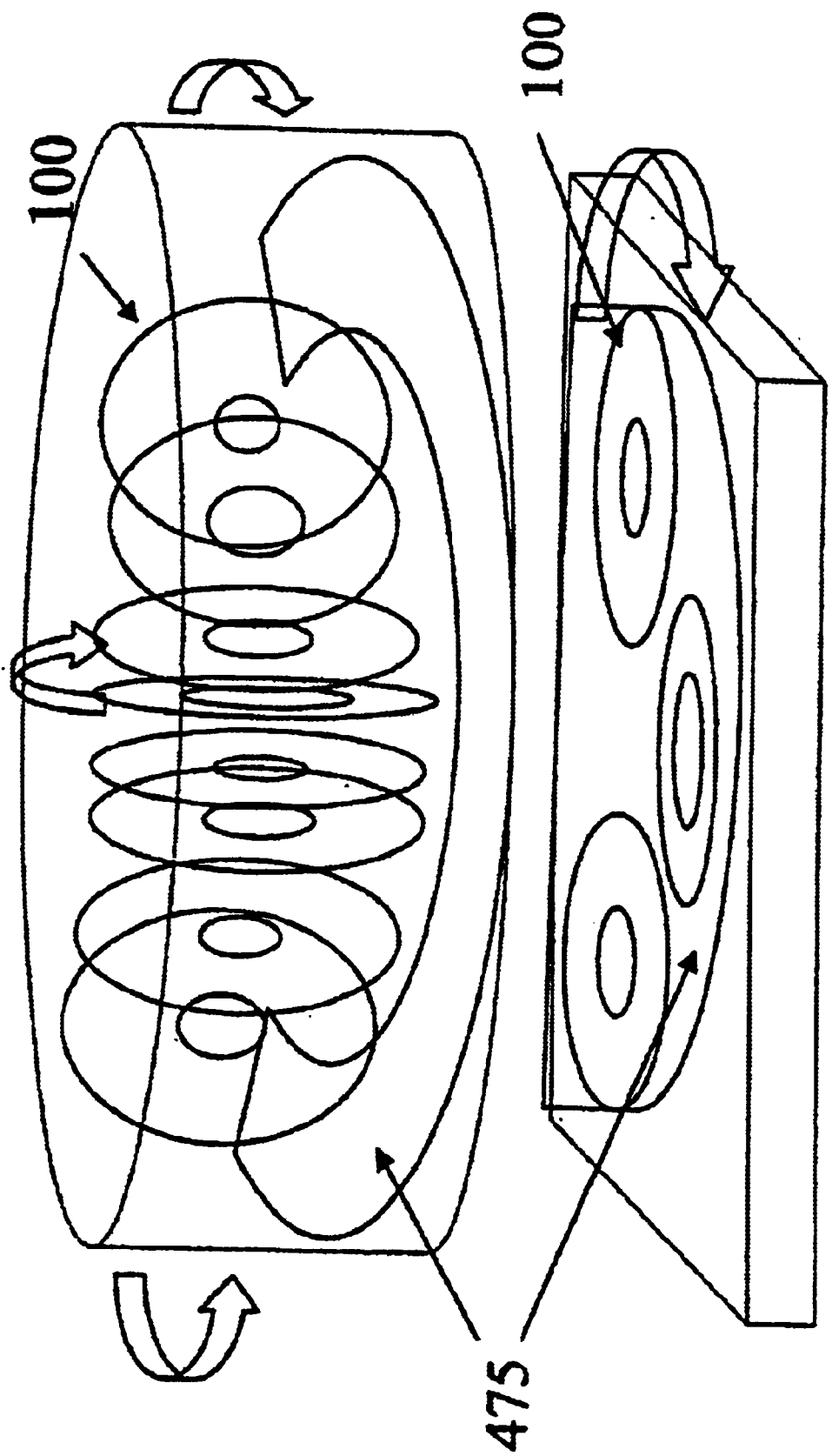
FIG. 15 depicts a cross-sectional'view of an alternate multimedia playback and scent recovery system made in accordance with a second preferred embodiment of the present invention for use in combination with an alternate multimedia and scent-bearing medium 100.

Another preferred embodiment of this invention as shown in FIG. 15, with the advantage of the scent recovery sequence information and multimedia information therein, illustrates another version of a multimedia playback and scent recovery system according to a preferred embodiment of the present invention by loading multiple scent disks 140 on the disk-like slots 475 within a jukebox-like embodiment.

Figure 16:
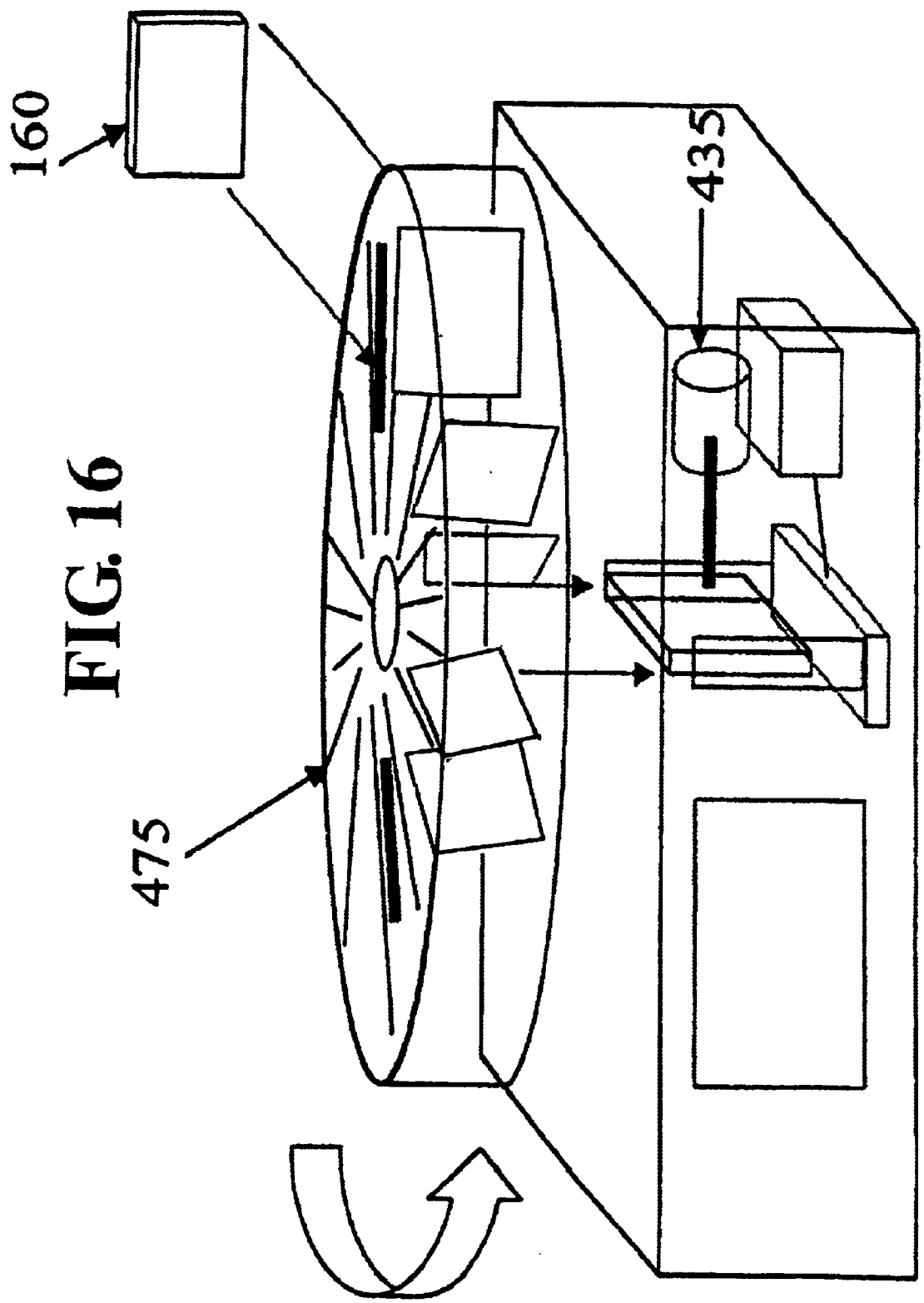
FIG. 16 depicts a cross-sectional view of an alternate multimedia playback and scent recovery system made in accordance with a second preferred embodiment of the present invention for use in combination with an alternate multimedia and scent-bearing medium 100.

Another preferred embodiment of this invention shown in FIG. 16, with the advantage of the scent recovery sequence information and multimedia information therein, illustrates another version of a multimedia playback and scent recovery system according to a preferred embodiment of the present invention by loading multiple scent cards 160 on card-like slots 475 within a slide projector-like embodiment.

In operation, the multimedia playback system 350 playback or recovers at least the tag information and/or a portion of the scent recovery sequence and multimedia information encoded on the multimedia storage medium 110 or from a remote multimedia source 390 through the input connection 385. The multimedia playback system 350 then transmits electronic signals to the controller 380 to generate scent control signals coupled with the tag information from the multimedia storage medium 110. Upon receipt of the control signals from the control signal generator 420, the controlled motor 440 that turns the scent disk 140, the movable heating element 430, and the controlled fan 460 are activated, thereby releasing the desired scent or combination of scents. The movable heating element 430 and the controlled fan 460 may be activated for an identical period of time, or for different lengths of time to release different strengths of their respective scents. In addition, the movable heating element 430 (e.g. Infrared or laser) only targets heat-releasable scents 230 within the inert storage medium 152 on the scent disk 140. The inert storage medium 152 will not interfere with the heat absorption process. Each of the systems in the scent recovery system 400 is deactivated in response to control signals transmitted by the control signal generator 420 to prevent any further scent release. When deactivated, the controlled motor 440, the movable heating element 430, and the controlled fan 460 are turned off. This process is repeated, as necessary, according to the scent recovery sequence and multimedia information encoded on the multimedia storage medium 110.

The foregoing description of the present invention has been presented for purposes of illustration and description. It is not intended to be exhaustive or to limit the invention to the precise form disclosed, and many modifications and variations are possible in light of the above disclosures.

What is claimed is:

1. A multimedia and scent-bearing disc for use in conjunction with a separate, integrated multimedia playback and scent recovery system, the multimedia and scent-bearing disc comprising:

a substrate for supporting multimedia and scent storage structures, the substrate circular in form;

a multimedia storage region positioned on the substrate for storing optically-encoded multimedia information;

a scent storage region positioned on the substrate for storing at least one scent; and digital playback control information comprising at least scent identification information for identifying the scent stored in the scent storage region, and playback control information for controlling the recovery of multimedia information and scent wherein the playback control information coordinates the playback of multimedia information and scent recovery to coincide with one another in a controlled and repeatable manner.

2. The multimedia and scent-hearing disc of claim 1 wherein the substrate for optically-encoding multimedia information permits overwriting of previous multimedia information with new multimedia information.

3. The multimedia and scent-bearing disc of claim 1 further comprising a storage case having sealing means for storing the multimedia and scent-bearing disc in a manner so that the scent is prevented from escaping.

4. The multimedia and scent-bearing disc of claim 1 further comprising a reusable gas impermeable membrane for placing over the scent storage region when the multimedia and scent-bearing disc is not in use to prevent the scent stored in the scent storage region from escaping.

5. The multimedia and scent-bearing disc of claim 1 wherein the digital playback control information is optically encoded in the multimedia storage region.

6. The multimedia and scent-bearing disc of claim 1 wherein the scent storage region stores a plurality of scents and wherein the digital playback control information identifies each of the plurality of scents that are stored in the scent storage region and their respective positions on the substrate.

7. The multimedia and scent-bearing disc of claim 6 wherein the scent-bearing region further comprises a scent-neutralizing material for use in neutralizing or masking scents previously released from the multimedia and scent-bearing disc.

8. The multimedia and scent-bearing disc of claim 6 wherein the scents are heat-releasable and wherein the scent storage region storing the plurality of scents further comprises:

a plurality of recessed three-dimensional regions each having an upwardly facing opening and each for storing a separate scent;

an inert storage medium deposited within he recessed three-dimensional regions for storing separate, heat-releasable scents deposited within the inert storage medium; and a gas permeable membrane placed over the upwardly-facing openings, wherein the gas-permeable membrane permits the scents to escape from the three-dimensional regions when the scents are heat-released.

9. The multimedia and scent-bearing disc of claim 8 wherein the gas permeable membrane comprises a microporous polymer.

10. The multimedia and scent-bearing disc of claim 8 wherein the gas permeable membrane comprises a macroporous polymer.

11. The multimedia and scent-bearing disc of claim 8 wherein the circular substrate is divided into two separate rings, an outer ring and an inner ring, and wherein the multimedia storage region occupies the inner ring and the scent storage region occupies the outer ring.

12. The multimedia and scent-bearing disc of claim 11 wherein the outer ring is divided into at least two sectors, and wherein at least one scent-storing recessed three-dimensional region occupies each of the sectors.

13. The multimedia and scent-bearing disc of claim 8 wherein the digital playback control information further comprises:
   scent recovery sequence information for controlling and sequencing the recovery and release of separate scents stored in the multimedia and scent-bearing region to coincide with different portions of the multimedia information during playback of the multimedia information.

14. The multimedia and scent-bearing disc of claim 13 wherein the multimedia information further comprises digitally-encoded audio information.

15. The multimedia and scent-beaing disc of claim 13 wherein the multimedia information further comprises digitally-encoded video information.

16. The multimedia and scent-bearing disc of claim 13 wherein the multimedia information further comprises digitally-encoded photographs.

17. The multimedia and scent-bearing disc of claim 13 wherein the multimedia information further comprises digitally-encoded textual information.

18. The multimedia and scent-bearing disc of claim 13 wherein the multimedia information further comprises digitally-encoded graphical information.

19. The multimedia and scent-bearing disc of claim 13 wherein the scent recovery sequence information further comprises multiple scent recovery information for controlling the simultaneous recovery of multiple scents.

20. The multimedia and scent-bearing disc of claim 13 wherein the multimedia information is segregated into separatly-recoverable segments for use with an interactive playback system.

21. The multimedia and scent-bearing disc of claim 20 wherein the scent recovery sequence information further comprises tag information for tagging particular scents to particular separately-recoverable multimedia segments.

22. A system for playback of multimedia information and recovery and release of scents for use in combination with the multimedia information comprising:
   a multimedia and scent-bearng disc comprising:
      a substrate for supporting structures containing multimedia information, scent and digital playback control information,
      a multimedia storage region positioned on the substrate for storing optically-encoded multimedia information;
      a scent storage region for storing at least one scent; and
      digital playback control information comprising at least scent identification information for identifying the scent stored in the storage region, and playback control information for controlling the recovery of multimedia information and scent, wherein the playback control information coordinates the playback of multimedia information and scent recovery to coincide with one another in a controlled and repeatable manner;
   a multimedia player and scent recovery system for use in conjunction with the separate multimedia and scent-bearng disc comprising:
      multimedia playback means for recovering the optically-encoded multimedia information stored in the multimedia storage region;
      scent recovery means for recovering and releasing the scents stored in the scent storage region;
      multimedia playback and scent recovery coordination means for recover the digital playback control information from the multimedia and scent-bearing disc and for using the digital playback control information in coordinating the simultaneous playback of multimedia information and recovery and release of scent from the multimedia and scent-bearing medium; and
      user input and control means for permitting the user of the system to input commands for controlling the playback of multimedia information and recovery of scents stored in the multimedia and scent-bearing disc.

23. The system of claim 22 wherein the multimedia information comprises audio information and wherein the multimedia playback means further comprises:
   an amplifier system for amplifying the audio signal recovered from the multimedia storage region; and
   a speaker system connected to the amplifier system.

24. The system of claim 22 where the digital playback and control information is optically encoded in the multimedia storage region.

25. The system of claim 22 further comprising local storage means for storing the multimedia signal recovered from the multimedia storage region of the multimedia and scent-bearing disc.

26. The system of claim 22 wherein the multimedia information is segregated into separately-recoverable segments for use with an interactive playback system.

27. The system of claim 26 wherein the scent recovery information further comprises tag information for tagging particular scents to particular separately-recoverable multimedia segments.

28. The system of claim 22 wherein the multimedia information comprises video information and wherein the multimedia playback means further comprises:
   a visual display means for viewing the video information recovered from the multimedia storage region.

29. The system of claim 28 wherein the visual display means comprises a monitor.

30. The system of claim 28 wherein the visual display means comprises an LCD display.

31. The system of claim 22 wherein the scent-bearing region of the multimedia and scent-bearing disc stores a plurality of scents.

32. The system of claim 31 wherein the digital playback control information further comprises scent recovery sequence information for controlling the sequential recovery of the plurality of scents stored in the multimedia and scent-bearing disc.

33. The system of claim 32 wherein the scent recovery means further comprises:
   a control signal generation means for interpreting the scent recovery sequence information and for converting the scent recovery sequence information into a control signal;

a moveable heating element, wherein the moveable heating element further comprises:

control signal reception means for receiving the control signal generated by the control signal generation means;

motor means for moving the heating element in dependence on the control signal to recover the next scent in sequence;

heating means for heating the scents stored in the scent storage region to release the scents; and ductwork immediately adjacent to the multimedia and scent-bearing disc wherein the scents released from the multimedia and scent-bearing disc may be vented to the user of the system.

34. The system of claim 33 wherein the scent recovery means further comprises:

a fan means for providing a positive pressure to assist in the venting of the released scents.

35. The system of claim 32 wherein the scent recovery means further comprises:

a control signal generation means for interpreting the scent recovery sequence information and for converting the scent recovery sequence information into a control signal;

a heating system further comprising:

multiple heating elements that are aligned with the separate scent storage regions of the multimedia an scent-bearing disc when the multimedia and scent-bearing disc is installed in the multimedia player and scent recovery system, wherein the multiple heating elements permit the simultaneous release of different scents from the scent storage region;

control signal reception means for receiving the control signal generated by the control signal generation means and for energizing the multiple heating elements in dependence on the control signal so that the scents are recovered from the multimedia and scent-bearing disc in the sequence encoded in the scent recovery sequence information; and ductwork immediately adjacent to the multimedia and scent-bearing disc wherein the scents released from the multimedia and scent-bearing disc may be vented to the user of the system.

36. The system of claim 35 wherein the scent recovery means further comprises:

a fan means for providing a positive pressure to assist in the venting of the released scents.

37. The system of claim 32 wherein the scent recovery sequence information specifies which scents should be recovered and released from the multimedia and scent-bearing disc.

38. The system of claim 37 wherein the scent recovery sequence information specifies the order in which scents are to be recovered and released from the multimedia and scent-bearing disc.

39. The system of claim 38 wherein the scent recovery sequence information specifies the duration of recovery and release of each of the scents recovered and released from the multimedia and scent-bearing disc.

40. The system of claim 32 wherein the multimedia player and scent recovery system further comprises:

means for storing the pre-programmed scent recovery sequence information; and scent recovery sequence information editing means for permitting the user to alter a pre-programmed scent recovery sequence stored in the multimedia and scent-bearing disc in order to create a user-specified scent recovery sequence.

41. The system of claim 40 wherein the pre-programmed scent recovery sequence information identifies which scents are to be recovered from the multimedia and scent-bearing disc; and wherein the scent recovery sequence information editing means permits the user to delete certain of the scents from the pre-programmed scent recovery sequence in order to create a user-specified scent recovery and release sequence.

42. The system of claim 40 wherein the pre-programmed scent recovery sequence information identifies which scents are to be recovered from the multimedia and scent-bearing disc and wherein the scent recovery sequence information editing means permits the user to add scents to the pre-programmed scent recovery and release sequence in order to create a user-specified scent recovery and release sequence.

43. The system of claim 42 wherein the scents added to the pre-programmed scent recovery sequence overlap in time other scents included in the pre-programmed scent recovery and release sequence.

44. The system of claim 40 further comprising:

user-specified scent recovery Sequence storage means for storing the user-specified scent recovery sequence created with the scent recovery sequence information editing means.

45. The system of claim 44 further comprising:

user-specified scent recovery sequence transmission means for transmitting the user-specified scent recovery sequence created with the scent recovery sequence information editing means to another user.

46. The system of claim 40 wherein the pre-programmed scent recovery sequence information identifies the duration of recovery of scents from the multimedia and scent-bearing disc and wherein the scent recovery sequence information editing means permits the user to alter the pre-programmned duration of scent recovery in order to create a user-specified scent recovery and release sequence.

47. The system of claim 46 wherein the pre-programmed scent recovery sequence information editing means permits the user to increase the duration of recovery of certain scents to be recovered from the multimedia and scent-bearing disc in order to create a user-specified scent recovery sequence.

48. The system of claim 46 wherein the pre-programmed scent recovery sequence information editing means permits the user to decrease the duration of recovery of certain scents to be recovered from the multimedia and scent-bearing disc in order to create a user-specified scent recovery and release sequence.

49. The system of claim 22 further comprising:

an input connection for accepting a multimedia signal from a remote source.

50. The system of claim 49 further comprising local storage means for storing the multimedia signal recovered from the remote source.

51. The system of claim 49 wherein the remote multimedia signal is segregated into separately-recoverable segments for use with an interactive playback system.

52. The system of claim 51 wherein the remote multimedia signal further comprises tag information for identifying which scents stored on the multimedia and scent-bearing disc are to be recovered in conjunction with the separately-recoverable multimedia segments.

53. The system of claim 49 wherein the remote multimedia signal further comprises:

scent recovery information for controlling the recovery of scents stored in the multimedia and scent-bearing disc.

54. The system of claim 53 wherein the remote multimedia signal further comprises a digitally-encoded video signal.

55. The system of claim 53 wherein the remote multimedia signal further comprises digitally-encoded photographs.

56. The system of claim 53 wherein the remote multimedia signal further comprises digitally-encoded textual information.

57. The system of claim 53 wherein the remote multimedia signal further comprises digitally-encoded graphical information.

58. The system of claim 53 wherein the remote multimedia signal further comprises a digitally-encoded audio signal.

59. The system of claim 58 wherein the audio signal is encoded in the MP3 format.

60. A system for use with a multimedia and scent-bearing medium and scent release and multimedia playback system wherein the scent release and multimedia playback system coordinates scent release from the multimedia and scent-bearing medium to coincide with multimedia playback in a precise, controllable and repeatable manner using pre-programmed digital scent release and multimedia playback information, the system comprising:

a memory for storing the pre-programmed digital scent release and multimedia playback information during an editing process;

an editing system for editing the pre-programmed digital scent release and multimedia playback information to create new scent release and multimedia playback information incorporating a different scent release and multimedia playback sequence than that encoded in the pre-programmed digital scent release and multimedia playback information, for use by the scent release and multimedia and playback system in recreating the scent release and multimedia playback sequence reflected in the new scent release and multimedia playback information; and storage means for storing the new multimedia playback and scent release information for future use by the scent release and multimedia playback system.

61. The system of claim 60 wherein the pre-programmed digital scent release and multimedia playback information identifies which scents are to be released from the multimedia and scent-bearing medium; and wherein the editing system permits a user to delete certain of the scents from the scent release sequence contained in the pre-programmed digital scent release and multimedia playback information in order to create a user-specified scent release sequence to be contained in the new digital scent release and multimedia playback information.

62. The system of claim 60 wherein the pre-programmed digital scent release and multimedia playback information identifies which scents are to be released from the multimedia and scent-bearing medium and wherein the editing system permits a user to add scents to the scent release sequence contained in the pre-programmed digital scent release and multimedia playback information in order to create a user-specified scent release sequence to be contained in the new digital scent release and multimedia playback information.

63. The system of claim 62 wherein the scents added to the pre-programmed scent recovery sequence overlap in time other scents included in the pre-programmed scent recovery sequence.

64. The system of claim 60 wherein the scent release information contained in the pre-programmed digital scent release and multimedia playback information identifies the duration of release of scents from the multimedia and scent-bearing medium and wherein the editing system permits a user to alter the pre-programmed duration of scent release in order to create a user-specified scent recovery sequence to be contained in the new digital scent release and multimedia playback information.

65. The system of claim 64 wherein the editing system permits the user to increase the duration of release of certain scents to be release from the multimedia and scent-bearing medium in order to create a user-specified scent recovery sequence to be contained in the new digital scent release and multimedia playback information.

66. The system of claim 64 wherein the editing system permits the user to decrease the duration of release of certain scents to be released from the multimedia and scent-bearing medium in order to create a user-specified scent recovery sequence to be contained in the new digital scent release and multimedia playback information.

* * * * *